(12) United States Patent
Coenen et al.

(10) Patent No.: US 7,335,150 B2
(45) Date of Patent: Feb. 26, 2008

(54) APPARATUS FOR MAKING PRE-FASTENED ABSORBENT UNDERGARMENTS

(75) Inventors: Joseph Daniel Coenen, Kaukauna, WI (US); Charles Robert Tomsovic, Omro, WI (US); Thomas E. Williamson, Appleton, WI (US); Brian Thomas Anderson, New London, WI (US); Scott Beck, Wild Rose, WI (US); Robin Nason, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 27 days.

(21) Appl. No.: 11/304,109

(22) Filed: Dec. 15, 2005

(65) Prior Publication Data

US 2007/0142194 A1   Jun. 21, 2007

(51) Int. Cl.
*B31F 1/10* (2006.01)
(52) U.S. Cl. ............ 493/418; 493/256; 493/359; 493/416
(58) Field of Classification Search .......... 493/243, 493/254, 256, 356, 357, 359, 405, 418, 424
See application file for complete search history.

(56) References Cited

U.S. PATENT DOCUMENTS

| 2,328,814 | A | * | 9/1943 | Laukhuff ............ 493/357 |
|---|---|---|---|---|
| 3,031,185 | A | | 4/1962 | Brien |
| 3,196,874 | A | | 7/1965 | Hrubecky |
| 3,552,736 | A | | 1/1971 | Frick et al. |
| 3,604,015 | A | | 9/1971 | Dove |
| 3,685,818 | A | | 8/1972 | Burger et al. |
| 3,724,464 | A | | 4/1973 | Enloe |
| 3,741,213 | A | | 6/1973 | Endres |
| 3,774,610 | A | | 11/1973 | Eckert et al. |
| 3,782,714 | A | | 1/1974 | Spencer et al. |
| 3,848,595 | A | | 11/1974 | Endres |

(Continued)

FOREIGN PATENT DOCUMENTS

EP    0 217 032 A2    4/1987

(Continued)

OTHER PUBLICATIONS

International Search Report for PCT/US2006/030034 dated Jan. 30, 2007, 3 pages.

(Continued)

*Primary Examiner*—Hemant M. Desai
(74) *Attorney, Agent, or Firm*—Armstrong Teasdale, LLP

(57) ABSTRACT

In a method and apparatus for mechanically fastening an absorbent undergarment during the initial manufacturing thereof, the undergarment is transported in a transport direction and folded longitudinally by a folding device such that first and second end regions of the undergarment are in generally opposed relationship with each other while transporting the partially assembled garment in the transport direction to fastenably engaged first and second fastening portions of the undergarment. A central region of the absorbent undergarment is held by a holding device, separate from the folding device, against bunching between the end regions of the undergarment during longitudinal folding of the undergarment. In another embodiment, the transverse position of the second fastening portion is adjusted relative to the first fastening portion to facilitate fastening engagement therebetween upon folding the absorbent garment longitudinally.

19 Claims, 20 Drawing Sheets

U.S. PATENT DOCUMENTS

| | | |
|---|---|---|
| 3,848,597 A | 11/1974 | Endres |
| 3,905,592 A | 9/1975 | Spencer et al. |
| 3,924,627 A | 12/1975 | Nystrand |
| 3,968,799 A | 7/1976 | Schrading |
| 3,994,486 A | 11/1976 | Nystrand |
| 4,029,310 A * | 6/1977 | Reist .......................... 493/426 |
| 4,519,596 A | 5/1985 | Johnson et al. |
| 4,648,861 A | 3/1987 | Pierce |
| 4,663,220 A | 5/1987 | Wisneski et al. |
| 4,704,116 A | 11/1987 | Enloe |
| 4,822,328 A | 4/1989 | Bertolini et al. |
| 4,940,464 A | 7/1990 | Van Gompel et al. |
| 5,046,272 A | 9/1991 | Vogt et al. |
| 5,104,116 A | 4/1992 | Pohjola |
| 5,110,403 A | 5/1992 | Ehlert |
| 5,176,615 A | 1/1993 | Munsch |
| 5,224,405 A | 7/1993 | Pohjola |
| 5,226,992 A | 7/1993 | Morman |
| 5,486,166 A | 1/1996 | Bishop et al. |
| 5,490,846 A | 2/1996 | Ellis et al. |
| 5,766,389 A | 6/1998 | Brandon et al. |
| 5,779,831 A | 7/1998 | Schmitz |
| 5,820,973 A | 10/1998 | Dodge, II et al. |
| 6,395,115 B1 | 5/2002 | Popp et al. |
| 6,409,858 B1 | 6/2002 | Popp et al. |
| 6,432,243 B1 | 8/2002 | Popp et al. |
| 6,447,628 B1 | 9/2002 | Couillard et al. |
| 6,481,362 B2 | 11/2002 | Hietpas et al. |
| 6,497,032 B2 | 12/2002 | Maxton et al. |
| 6,513,221 B2 | 2/2003 | Vogt et al. |
| 6,514,187 B2 | 2/2003 | Coenen et al. |
| 6,562,167 B2 | 5/2003 | Coenen et al. |
| 6,565,691 B2 | 5/2003 | Tomsovic et al. |
| 6,596,113 B2 | 7/2003 | Csida et al. |
| 6,723,034 B2 * | 4/2004 | Durrance et al. ........... 493/373 |
| 6,821,370 B2 * | 11/2004 | Tomsovic et al. ........... 156/200 |
| 7,069,970 B2 * | 7/2006 | Tomsovic et al. ........... 156/444 |
| 2003/0111168 A1 | 6/2003 | Olson et al. |
| 2003/0205312 A1 | 11/2003 | Tomsovic et al. |

FOREIGN PATENT DOCUMENTS

| | | |
|---|---|---|
| EP | 0 701 424 B1 | 3/1996 |
| EP | 1504738 A2 | 2/2005 |
| EP | 1552798 A1 | 7/2005 |
| JP | 7-205943 | 8/1995 |
| WO | WO 95/32639 A1 | 12/1995 |
| WO | WO 00/37009 A2 | 6/2000 |
| WO | WO 01/87206 A1 | 11/2001 |
| WO | WO 01/87216 A1 | 11/2001 |
| WO | WO 01/87217 A2 | 11/2001 |
| WO | WO 01/87218 A2 | 11/2001 |
| WO | WO 01/87753 A2 | 11/2001 |
| WO | WO 02/00152 A1 | 1/2002 |
| WO | WO 02/065961 A2 | 8/2002 |
| WO | WO 02/067835 A2 | 9/2002 |
| WO | WO 03/041624 A1 | 5/2003 |
| WO | WO 03/051247 A2 | 6/2003 |
| WO | WO 03/051248 A2 | 6/2003 |
| WO | WO 03/053321 A1 | 7/2003 |

OTHER PUBLICATIONS

International Search Report for PCT/US2006/015228, dated Aug. 23, 2006, 4 pages.

* cited by examiner

# APPARATUS FOR MAKING PRE-FASTENED ABSORBENT UNDERGARMENTS

BACKGROUND

The present invention relates generally to apparatus and methods for making pre-assembled or pre-fastened absorbent undergarments, and more particularly to apparatus and methods for engaging cooperating fastening components of pre-fastened absorbent undergarments during the making of such undergarments.

Absorbent undergarments have numerous applications including, without limitation, diapers, training pants and adult incontinence products. A typical absorbent undergarment is formed as a composite structure including an absorbent assembly disposed between a liquid permeable bodyside liner and an outer cover. These components can be combined with other materials and features such as elastic materials and containment structures to form a product which is specifically suited to its intended purposes. A number of such undergarments include fastening components which are intended to be secured together (e.g., pre-fastened) during manufacture of the garment so that the product is packaged in it's fully assembled, ready-to-wear form.

As an example, a child's training pants conventionally has a central absorbent chassis and front and back side panels extending laterally out from the chassis adjacent longitudinally opposite ends thereof. Each of the front and back side panels has a fastening component thereon, such as a hook or a loop fastener. During manufacture of the training pants, the central absorbent chassis is initially formed generally flat and then folded over so that the front and back side panels face each other. The respective fastening components of the front and back side panels are then aligned and engaged with each other to pre-fasten the training pants in its fully assembled three-dimensional form.

However, existing techniques for making conventional absorbent undergarments such as the training pants described above or other pre-fastened undergarments in which fastening components are pre-fastened together during manufacture are in some respects inadequate. In particular, typical manufacturing processes are performed at high speeds, such as to make 250 or more pre-fastened absorbent undergarments per minute. One sometimes limiting factor is that folding of the undergarment while the garment is being moved along the machine direction at high speed requires reciprocating movement of a folding device in a direction orthogonal to the direction in which the undergarment web is moving. This can result in inconsistent locating of the fold line along which the garment is folded. Commonly used processes also require multiple stations along the manufacturing apparatus, such as one station at which the garment is folded and a separate station at which the side panels are subsequently fastened together. Specifically, multiple stations must be used so as to avoid any of the folding and engaging devices of the manufacturing line from becoming disposed within the interior of the pre-fastened garment as it is folded and fastened, thereby inhibiting further movement of the garment along the line.

To this end, Japanese Laid-Open Patent Application No. 7-205943 discloses a folding device in which multiple pairs of suction folding means are provided on a rotating drum, with each pair of suction folding means being capable of both folding one absorbent garment and attaching the side edges of the garment together. In particular, as the drum rotates a respective pair of the suction folding means is in an open configuration in which the folding means are laid flat, or tangent relative to the rotating drum. In this configuration, a garment that has been cut from a web of such garments is suctioned flat onto the pair of suction folding means. Upon further rotation of the drum, adhesive is applied to the side edges of the garment. Further rotation of the drum causes the pair of suction folding means to fold inward toward each other while the garment is still suctioned to the respective folding means. The garment is thus folded in half to bring the ends of the garment together. The edges of the garment contact each other such that the adhesive holds the edges together in what is commonly referred to as a butt-seam. Finally, the drum is rotated to a position in which the suction folding means are opened again, whereby suction to one of the folding means is decreased so that the folded garment is held only by the other folding means and then transferred to a conveyor for further processing.

While such a folding device is intended to increase the processing speed for making folded undergarments, butt-seams generally present an unfinished appearance. More desirable is what is commonly referred to as a lap seam in which the side edges of the garment at one end thereof overlap and are engaged with the side edges of the garment at the opposite end of the garment. Moreover, the central or crotch region of the garment spans the two suction folding means and is otherwise unretained against movement relative to the folded portions of the garment. As a result, the central region of the garment may undesirably move or creep up between the folding means in reaction to folding of the garment.

As another example, U.S. Pat. No. 5,779,831 discloses an apparatus that grips an unfolded undergarment in four locations and folds the undergarment in half. The gripped portions of the undergarment are then folded inward toward each other. As a result, portions of the undergarment adjacent to the gripped portions overlap each other and are bonded together by an ultrasonic bonding device. However, the portions of the undergarment that are to be bonded together are ungripped (i.e., the overlapping portions adjacent the gripped portions) and are therefore not positively held in opposed relationship. There is a risk that motion of the apparatus or other surrounding conditions can cause the portions that are to be bonded to become misaligned, folded or the like and result in a less than desirable bonding.

Also, while various other apparatus and processes for forming lap seams are known to those skilled in the art, such apparatus and processes typically require the lap seam forming to be conducted other than at the same station at which the folding of the garment occurs. As such, additional processing apparatus and time is needed to make such a lap seam.

SUMMARY

In one embodiment, apparatus for mechanically fastening an absorbent undergarment to reconfigure the undergarment from a partially assembled, unfastened configuration to a pre-fastened configuration during the initial manufacturing thereof generally comprises a transport device driven to move in a transport direction and a longitudinal folding device carried by the transport device in the transport direction. The longitudinal folding device is configurable relative to the transport device between an open configuration in which the longitudinal folding device receives an absorbent undergarment in its partially assembled configuration, and a closed configuration in which the absorbent undergarment is folded longitudinally by the folding device.

The longitudinal folding device comprises first and second folding plates moveable relative to each other between the open and closed configurations of the folding device. In the closed configuration of the folding device the folding plates are in opposed relationship with each other and in the open configuration of the folding device the plates are out of opposed relationship with each other. The folding plates each have an inner end and an outer end, with the inner ends of the folding plates being nearer to each other than the outer ends of the folding plates in the open configuration of the folding device. The inner ends of the folding plates are spaced from each other in the open configuration of the folding device.

The first folding plate is adapted to retain a first end region of the absorbent undergarment thereon and the second plate is adapted to retain a second end region of the absorbent undergarment thereon such that the central region of the absorbent undergarment is generally adjacent the inner ends of the folding plates and spans the spacing between the inner ends. The folding device is configured such that in the closed configuration of the folding plates, first and second fastening portions of the undergarment are brought together for fastening engagement therebetween. A holding device separate from the first and second folding plates is disposed generally intermediate the inner ends of the folding plates and is adapted to position the central region of the absorbent undergarment longitudinally outward of the inner ends of the folding plates in the closed configuration of the folding device.

In another embodiment, apparatus for mechanically fastening an absorbent undergarment to reconfigure the undergarment from a partially assembled, unfastened configuration to a pre-fastened configuration during the initial manufacturing thereof generally comprises a transport device driven to move in a transport direction and a longitudinal folding device carried by the transport device in the transport direction. The longitudinal folding device is configurable relative to the transport device between an open configuration in which the longitudinal folding device receives an absorbent undergarment in its partially assembled configuration, and a closed configuration in which the absorbent undergarment is folded longitudinally by the folding device. The longitudinal folding device comprises first and second folding plates moveable relative to each other between the open and closed configurations of the folding device, wherein in the closed configuration of the folding device the folding plates are in opposed relationship with each other and in the open configuration of the folding device the plates are out of opposed relationship with each other.

A transverse retention member is generally adjacent to the second folding plate and is adapted to retain a second fastening portion of the undergarment thereon upon movement of the folding plates from the open configuration of the folding device to the closed configuration thereof. The transverse retention member is moveable at least transverse to the second folding plate to adjust the transverse position of the second fastening portion of the undergarment relative to the second folding plate to facilitate fastening engagement of the second fastening portion of the undergarment with a first fastening portion thereof in the closed configuration of the folding device.

In general, one embodiment of a method for mechanically forming a pre-fastened absorbent undergarment during initial manufacture of the undergarment comprises partially assembling the absorbent undergarment to have a configuration in which the undergarment is generally unfolded and first and second fastening portions are unfastened. The absorbent undergarment is transported in a transport direction and folded longitudinally such that first and second end regions of the undergarment are in generally opposed relationship with each other while transporting the partially assembled garment in the transport direction. A central region of the absorbent garment is held against bunching between the first and second end regions of the undergarment during longitudinal folding of the absorbent undergarment while transporting the undergarment in the transport direction.

In another embodiment, such a method generally comprises partially assembling an absorbent undergarment to have a configuration in which the undergarment is generally unfolded and first and second fastening portions are unfastened. The absorbent undergarment is transported in a transport direction and folded longitudinally such that first and second end regions of the undergarment are in generally opposed relationship with each other while transporting said partially assembled garment in the transport direction. The transverse position of the second fastening portion of the undergarment is adjusted relative to the first fastening portion to facilitate fastening engagement with the first fastening portion of the undergarment upon folding the absorbent garment longitudinally, said adjusting step being performed while transporting the undergarment in the transport direction.

BRIEF DESCRIPTION OF THE DRAWINGS

Corresponding reference characters indicate corresponding parts throughout the drawings.

DETAILED DESCRIPTION

The methods and apparatus set forth herein may be used to make a variety of absorbent undergarments including, without limitation, diapers, training pants, feminine hygiene products, incontinence products, medical garments, other personal care or health care garments, swim pants, athletic clothing, pants and shorts, and the like. For ease of explanation, these methods and apparatus are hereafter particularly described in connection with making pre-fastened childrens' training pants, generally indicated as 20 in FIG. 1. In particular, the methods and apparatus will be described in terms of those for making pre-fastened disposable training pants similar to the pants described in published PCT Application No. WO 00/37009, published Jun. 29, 2000 by A. L. Fletcher et al., the disclosure of which is incorporated herein by reference. The training pants 20 may also be constructed using the methods and apparatus disclosed in U.S. Pat. No. 4,940,464 issued Jul. 10, 1990 to VanGompel et al.; and U.S. Pat. No. 5,766,389 issued Jun. 16, 1998 to Brandon et al.; the disclosures of which are also incorporated herein by reference.

Figure 1:
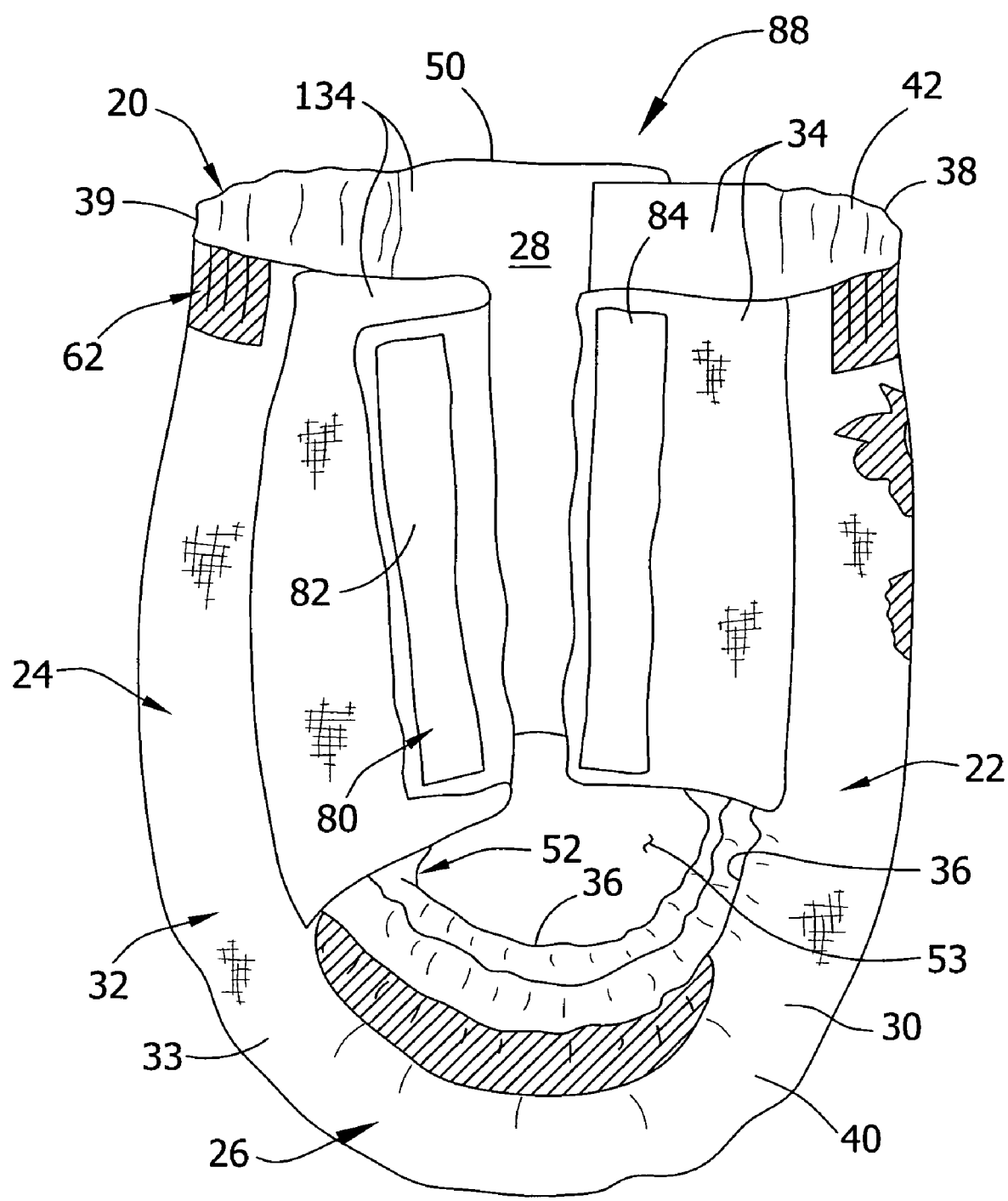
FIG. 1 is a side elevation of on embodiment of an absorbent undergarment in the form of a child's training pants with a fastening system of the training pants shown fastened on one side of the training pants and unfastened on the opposite side of the training pants.

With reference now to the drawings, and in particular to FIG. 1, the training pants 20 are illustrated in a partially fastened condition and comprise an absorbent chassis 32 and a fastening system 80. The absorbent chassis 32 has a front waist region 22 (broadly, a first longitudinal end region), a back waist region 24 (broadly, a second longitudinal end region), and a crotch region 26 (broadly, a central region) extending between and interconnecting the front and back waist regions, an inner surface 28 which faces the wearer, and an outer surface 30 which is opposite the inner surface and faces away from the wearer. With additional reference to FIGS. 2 and 3, the absorbent chassis 32 also has a pair of laterally opposite side edges 36 and a pair of longitudinally opposite waist edges, respectively designated front waist edge 38 and back waist edge 39. The front waist region 22 is contiguous with the front waist edge 38, and the back waist region 24 is contiguous with the back waist edge 39.

Figure 2:
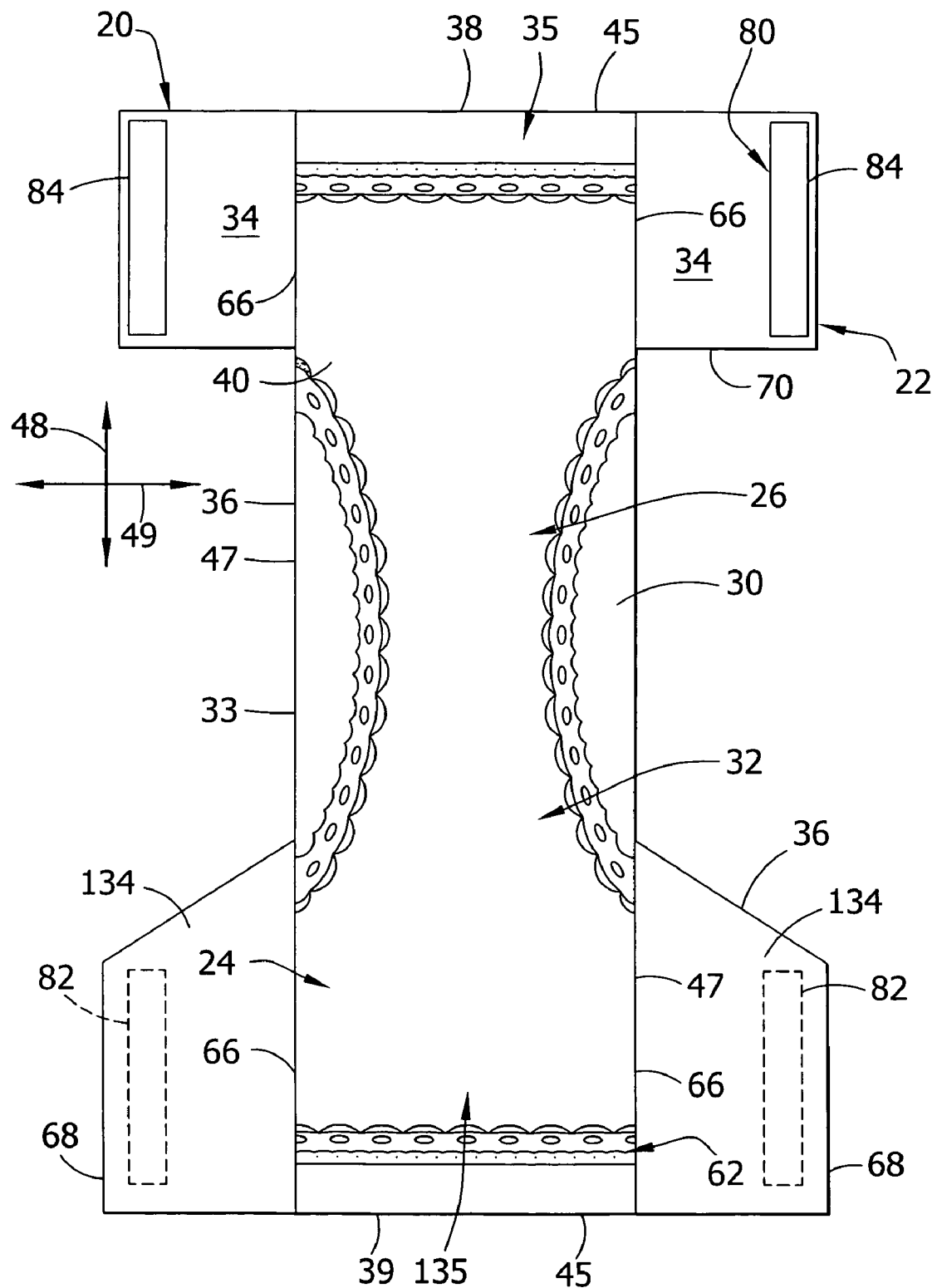
FIG. 2 is a bottom plan view of the training pants of FIG. 1 in an unfastened, unfolded and laid flat condition to show the surface of the training pants which faces away from the wearer.
Figure 3:
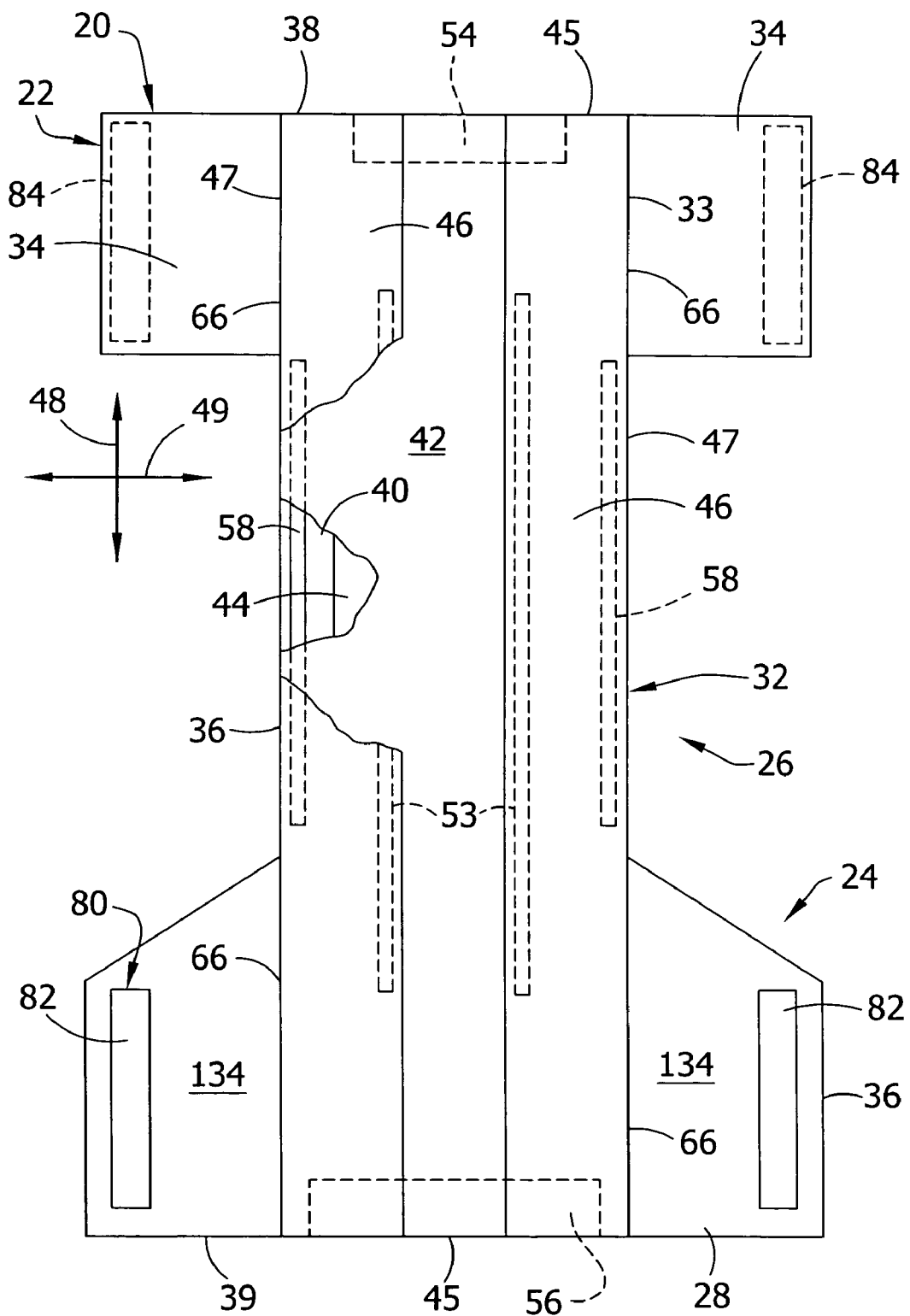
FIG. 3 is a top plan view of the training pants it its unfastened, unfolded and laid flat condition to show the surface of the training pants which faces the wearer, with portions of the training pants being cut away to reveal underlying features.

The illustrated absorbent chassis 32 comprises a composite structure 33 which when laid flat can be rectangular or any other desired shape, and has a pair of laterally opposite front side panels 34 and a pair of laterally opposite back side panels 134 extending outward therefrom. The composite structure 33 and side panels 34 and 134 may comprise two or more separate elements, as shown in FIG. 1, or be integrally formed. Integrally formed side panels 34, 134 and composite structure 33 would comprise at least some common materials, such as the bodyside liner, flap composite, outer cover, other materials and/or combinations thereof, and/or could define a one-piece elastic, stretchable, or non-stretchable pants. The illustrated composite structure 33 comprises an outer cover 40, a bodyside liner 42 (FIGS. 1 and 3) which is connected to the outer cover in a superposed relation, an absorbent assembly 44 (FIG. 3) which is located between the outer cover and the bodyside liner, and a pair of containment flaps 46 (FIG. 3). The illustrated composite structure 33 has opposite ends 45 which form portions of the front and back waist edges 38 and 39, and opposite side edges 47 which form portions of the side edges 36 of the absorbent chassis 32 (FIGS. 2 and 3). For reference, arrows 48 and 49 depict the orientation of the longitudinal axis and the transverse or lateral axis, respectively, of the training pants 20.

With the training pants 20 in the fastened position as partially illustrated in FIG. 1, the front and back side panels 34, 134 are secured together to define a three-dimensional pants configuration having a waist opening 50, a pair of leg openings 52 and an interior space 53. The front waist region 22 comprises the portion of the training pants 20 which, when worn, is positioned on the front of the wearer while the back waist region 24 comprises the portion of the training pants which, when worn, is positioned on the back of the wearer. The crotch region 26 of the training pants 20 comprises the portion of the training pants 20 which, when worn, is positioned between the legs of the wearer and covers the lower torso of the wearer. The front and back side panels 34 and 134 comprise the portions of the training pants 20 which, when worn, are positioned on the hips of the wearer. The waist edges 38 and 39 of the absorbent chassis 32 are configured to encircle the waist of the wearer when worn and together define the waist opening 50 (FIG. 1). Portions of the side edges 36 in the crotch region 26 generally define the leg openings 52.

The absorbent chassis 32 is configured to contain and/or absorb any exudates discharged from the wearer. For example, the absorbent chassis 32 desirably although not necessarily has a pair of containment flaps 46 (FIG. 3) which are configured to provide a barrier to the transverse flow of body exudates. A flap elastic member 53 (FIG. 3) can be operatively joined with each containment flap 46 in any suitable manner as is well known in the art. The elasticized containment flaps 46 define an unattached edge which assumes an upright configuration in at least the crotch region 26 of the training pants 20 to form a seal against the wearer's body. The containment flaps 46 can be located along the side edges 36 of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 desirably although not necessarily include a front waist elastic member 54, a rear waist elastic member 56, and leg elastic members 58, as are known to those skilled in the art. The waist elastic members 54 and 56 can be operatively joined to the outer cover 40 and/or the bodyside liner 42 along the opposite waist edges 38 and 39, and can extend over part or all of the waist edges. The leg elastic members 58 can be operatively joined to the outer cover 40 and/or the bodyside liner 42 along the opposite side edges 36 and positioned in the crotch region 26 of the training pants 20. The leg elastic members 58 can be longitudinally aligned along each side edge 47 of the composite structure 33.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic constrictive forces are imparted to the substrate.

The outer cover 40 suitably comprises a material which is substantially liquid impermeable, and can be elastic, stretchable or nonstretchable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive, ultrasonic bonds, thermal bonds, or the like. Suitable laminate adhesives can be applied continuously or intermittently as beads, a spray, parallel swirls, or the like. The liquid permeable outer layer can be any suitable material and desirably one that provides a generally cloth-like texture. The inner layer of the outer cover 40 can be both liquid and vapor impermeable, or can be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and caregiver.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness. Alternatively, the bodyside liner 42 can be more hydrophilic or can have essentially the same affinity for moisture as the absorbent assembly 44 to present a relatively wet surface to the wearer to increase the sensation of being wet. This wet sensation can be useful as a training aid. The hydrophilic/hydrophobic properties can be varied across the length, width and depth of the bodyside liner 42 and absorbent assembly 44 to achieve the desired wetness sensation or leakage performance.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. The outer cover 40, bodyside liner 42 and other materials used to construct the pants may comprise elastomeric or nonelastomeric materials.

The absorbent assembly 44 (FIG. 3) is positioned between the outer cover 40 and the bodyside liner 42, which can be joined together by any suitable means such as adhesives, ultrasonic bonds, thermal bonds, or the like. The absorbent assembly 44 can be any structure which is generally compressible, conformable, non-irritating to the child's skin, and capable of absorbing and retaining liquids and certain body wastes, and may be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Typically, a superabsorbent material is capable of absorbing at least about 15 times its weight in water, and desirably is capable of absorbing more than about 25 times its weight in water. As a general rule, the superabsorbent material is present in the absorbent assembly 44 in an amount of from 0 to about 90 percent weight based on total weight of the absorbent assembly. The absorbent assembly 44 may or may not be wrapped or encompassed by a suitable tissue wrap that may help maintain the integrity and/or shape of the absorbent assembly.

The absorbent chassis 32 can also incorporate other materials designed primarily to receive, temporarily store, and/or transport liquid along the mutually facing surface with absorbent assembly 44, thereby maximizing the absorbent capacity of the absorbent assembly. One suitable material is referred to as a surge layer (not shown) and may be located adjacent the absorbent assembly 44 (e.g., between the absorbent assembly and the liner 42) and attached to various components of the article 20 such as the absorbent assembly and/or the bodyside liner 42 by methods known in the art, such as by adhesive, ultrasonic or thermal bonding. A surge management layer helps to decelerate and diffuse surges or gushes of liquid that may be rapidly introduced into the absorbent assembly 44. Desirably, the surge management layer can rapidly accept and temporarily hold the liquid prior to releasing the liquid into the storage or retention portions of the absorbent assembly 44. Examples of suitable surge management layers are described in U.S. Pat. Nos. 5,486,166; and 5,490,846. Other suitable surge management materials are described in U.S. Pat. No. 5,820,973. The entire disclosures of these patents are incorporated by reference herein.

As noted previously, the front and back side panels 34 and 134 are disposed on laterally opposite sides of the absorbent chassis 32 in longitudinally spaced relationship with each other. The front side panels 34 can be permanently bonded along seams 66 to the composite structure 33 of the absorbent chassis 32 in the respective front and back waist regions 22 and 24. More particularly, as seen best in FIGS. 2 and 3, the front side panels 34 can be permanently bonded to and extend transversely outward beyond the side edges 47 of the composite structure 33 in the front waist region 22, and the back side panels 134 can be permanently bonded to and extend transversely outward beyond the side edges of the composite structure in the back waist region 24. The side panels 34 and 134 may be bonded to the composite structure 33 using attachment means known to those skilled in the art such as adhesive, thermal or ultrasonic bonding. Alternatively, the side panels 34 and 134 can be formed as an integral portion of a component of the composite structure 33. For example, the side panels can comprise a generally wider portion of the outer cover 40, the bodyside liner 42, and/or another component of the absorbent chassis 32. The front and back side panels 34 and 134 can be permanently bonded together or be releasably engaged with one another as illustrated by the fastening system 80.

The side panels 34, 134 may, but need not necessarily, comprise an elastic material capable of stretching in a direction generally parallel to the transverse axis 49 of the training pants 20. Suitable elastic materials, as well as one process of incorporating elastic side panels into training pants, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may comprise other woven or nonwoven materials, such as those described above as being suitable for the outer cover 40 or bodyside liner 42; mechanically pre-strained composites; or stretchable but inelastic materials.

The illustrated training pants 20 includes the fastening system 80 for refastenably securing the training pants about the waist of the wearer. The illustrated fastening system 80 includes first fastening components 84 adapted for refastenable engagement to corresponding second fastening components 82. In one embodiment, one surface of each of the first fastening components 84 comprises a plurality of engaging elements which project from that surface. The engaging elements of the first fastening components 84 are adapted to repeatedly engage and disengage engaging elements of the second fastening components 82.

The fastening components 84, 82 can comprise separate elements bonded to the side panels 34, 134, or they may be integrally formed with the side panels. Thus, unless otherwise specified, the term "fastening component" includes separate components which function as fasteners, and regions of materials such as side panels which function as fasteners. Moreover, a single material can define multiple fastening components to the extent that different regions of the material function as separate fasteners. The fastening components 84, 82 can be located on the side panels 34, 134, between the side panels such as on the absorbent chassis, or a combination of the two. The fastening components 84, 82 can comprise any refastenable fasteners suitable for absorbent articles, such as adhesive fasteners, cohesive fasteners, mechanical fasteners, or the like. In particular embodiments the fastening components comprise mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated embodiment, the first fastening components 84 comprise hook fasteners and the second fastening components 82 comprise complementary loop fasteners. In another particular embodiment, the first fastening components 84 comprise loop fasteners and the second fastening components 82 comprise complementary hook fasteners. Alternatively, the fastening components 84, 82 may comprise interlocking similar surface fasteners, adhesive or cohesive fastening elements such as an adhesive fastener and an adhesive-receptive landing zone or material; or the like. Although the training pants 20 illustrated in FIG. 1 show the back side panels 134 overlapping the front side panels 34, the training pants 20 may instead be configured so that the front side panels overlap the back side panels.

With particular reference to FIG. 2, the fastening components 84 are disposed on the outer surface 30 of the front side panels 34. The fastening components 84 are sized to receive the fastening components 82 and are suitably positioned along the outer edges of the front side panels 34 to broadly define laterally spaced front or first fastening portions at the front or first end region 22 of the pants 20. With particular reference to FIG. 3, the fastening components 82 are disposed on the inner surface 28 of the back side panels 134. The fastening components 82 are suitably positioned along the laterally outer edges of the back side panels 134 and broadly define laterally spaced back or second fastening portions at the back or second end region 24 of the pants 20. It is understood that the fastening components 82, 84 may also extend laterally out beyond the outer edges of the side panels 134, 34. Where the first fastening components 82 comprise loop fasteners disposed on the inner surface 28 and the second fastening components 84 comprise hook fasteners disposed on the outer surface 30, the first fastening components can be sized larger than the second fastening components to ensure coverage of the outwardly-directed hooks. As used herein, the term fastening portion is intended to broadly refer to those portions of the garment that are to be overlapped with and fastenably engaged with each other to form the pre-fastened (e.g., three dimension ready-to-wear) configuration of the pants 20.

The fastening components 84, 82 can be adhered to the respective side panels 34, 134 by any means known to those skilled in the art such as adhesive bonds, ultrasonic bonds, thermal bonds and pressure bonds. The fastening components 84, 82 may comprise separate fastening elements or distinct regions of an integral material. For example, the training pants 20 can include an integral second fastening material disposed in the front waist region 22 for refastenably connecting to the first fastening components 82 at two or more different regions, which define the second fastening components 84 (FIG. 1). In a particular embodiment, the fastening components 82, 84 can comprise integral portions of the waist regions 24, 22. For instance, one of the elastomeric front or back side panels 34, 134 can function as second fastening components 84 in that they can comprise a material which is releasably engageable with fastening components 82 disposed in the opposite waist region.

When engaged, the illustrated fastening components 82, 84 (and more suitably the front and back fastening portions) of the pants 20 define refastenable engagement seams 88 (FIG. 1). For the engagement seams 88 to be located at the sides of the wearer, it can be particularly desirable for the transverse distance between the fastening components 82 of the back side panels 134 to be substantially equal to the transverse distance between the fastening components 84 of the front side panel 134. The transverse distance between a set of fastening components 82, 84 is measured parallel to the transverse axis 49 between the longitudinal center lines of the fastening component, measured with the side panels 34, 134 in an unstretched condition. Alternatively, the lateral spacing between the fastening components 82 may be greater or less than the lateral spacing between the fastening components 84. It is also contemplated that fastening components 82 (and/or the fastening components 84) may not be laterally opposite each other, or may only be partially laterally opposite each other, such as by being offset longitudinally, without departing from the scope of this invention.

Figure 4:
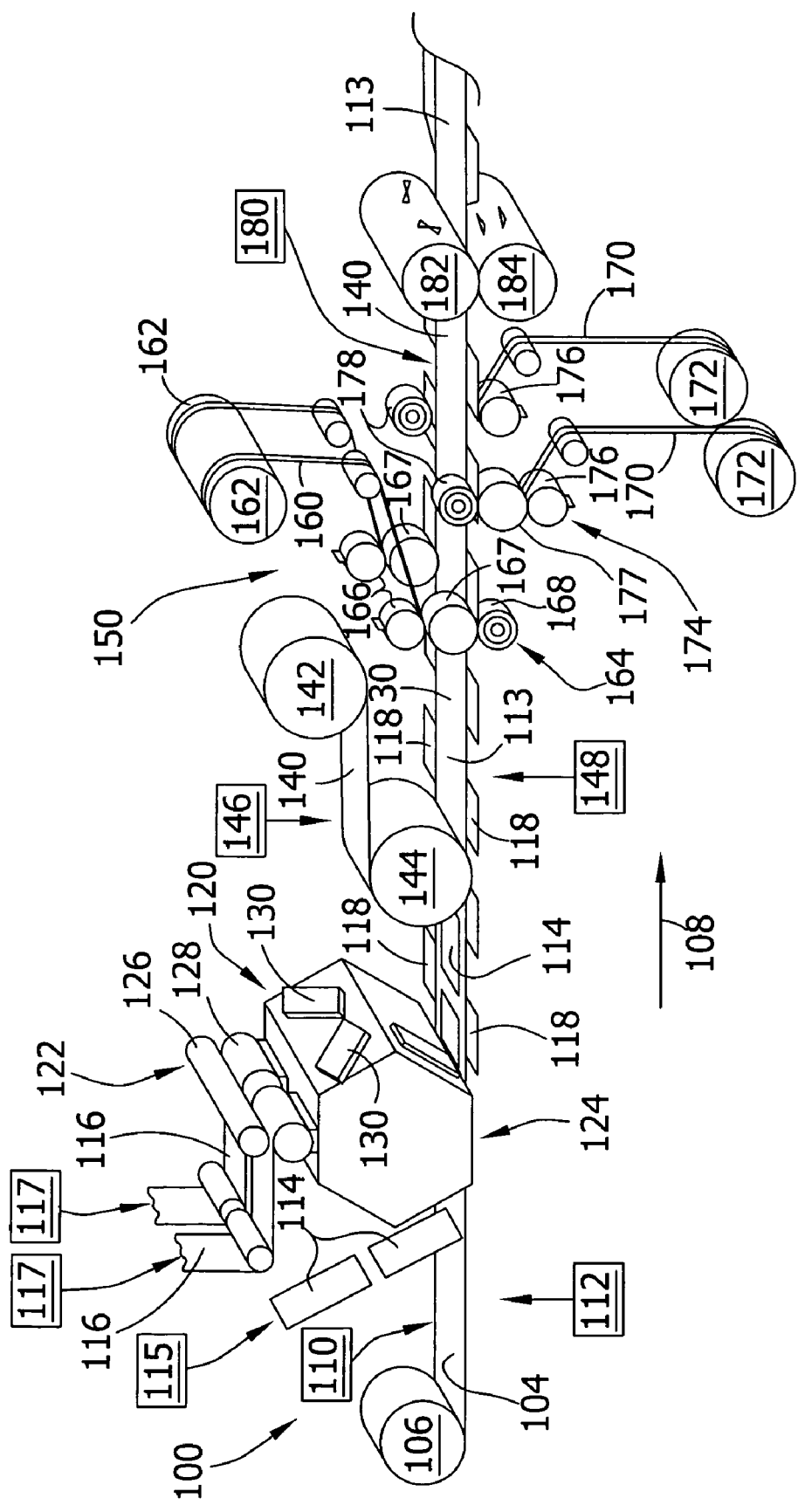
FIG. 4 is a schematic of an assembly system for making absorbent undergarments such as the training pants of FIGS. 1-3.

FIG. 4 generally illustrates one embodiment of a suitable assembly system, generally indicated at 100, for assembling a continuous web of absorbent undergarments to be subsequently cut into discrete undergarments such as the training pants 20 of FIGS. 1-3 and then pre-fastened together in their fully assembled or pre-fastened configuration. The various components of the training pants 20 can be secured together in the assembly system 100 by any means known to those skilled in the art such as, for example, adhesive, thermal and/or ultrasonic bonds. Certain garment manufacturing equipment which is readily known and understood in the art, including frames and mounting structures, ultrasonic and adhesive bonding devices, transport conveyors, transfer rolls, guide rolls, tension rolls, and the like, are well know in the art and have not been illustrated in FIG. 4. As an example, suitable absorbent supply mechanisms, web unwinds, conveyor systems, registration systems, drive systems, control systems and the like are disclosed in U.S. Pat. No. 5,766,389 issued Jun. 16, 1998 to Brandon et al., the entire disclosure of which is incorporated herein by reference.

With particular reference to the assembly system 100 illustrated in FIG. 4, a continuous supply of material 104 used to form the bodyside liner 42 is provided from a supply source 106. The supply source 106 can comprise for example any standard unwind mechanism, which generally includes a pair of spindles, a festoon assembly, and a dancer roll for providing bodyside liner material 104 at a desired speed and tension. Various components can be disposed on and/or bonded to the bodyside liner material 104 as the material travels in a machine direction identified by arrow 108. In particular, a surge layer can be provided at an application station 110 and disposed on and/or bonded to the bodyside liner material 104. The surge layer can comprise either a continuous web or discrete sheets. Additionally, a containment flap module 112 can be provided downstream from the supply source 106 for attaching pre-assembled containment flaps to the bodyside liner material 104. As various components are added in the assembly system 100, a continuously moving product assemblage 113 is formed.

A plurality of absorbent assemblies 114 can be provided from a suitable supply source 115. The supply source 115 can be any conventional mechanism for supplying the absorbent assemblies 114. Generally, a conventional supply source can include a hammermill for forming fluff fibers and, if desired, for providing an enclosure for mixing superabsorbent material with the fluff fibers, and then depositing the fluff and superabsorbent material on a forming drum having a desired absorbent design. The individual absorbent assemblies 114 can be disposed intermittently on the continuously moving bodyside liner material 104, one for each pair of training pants. The position of the absorbent assemblies 114 can be registered with the position of the surge material, if employed. The absorbent assemblies 114 can be bonded to one or more other components using adhesives or other suitable means. Alternatively, composite absorbent materials can be fed into the converting process from rolls or compressed packages, such as festooned bales.

Continuous-webs of material 116 used to form the side panels 34, 134 can be provided from suitable supply sources 117. The supply sources 117 can comprise one or more standard unwind mechanisms. The side panel material 116 can be cut into individual strips 118 and positioned partially on the bodyside liner material 104 using an applicator device 120. In the cross machine direction,-the individual strips 118 desirably extend laterally outward from the bodyside liner material 104 (see FIGS. 4 and 7) and overlap the bodyside liner material by an amount such as about 2 or more centimeters to permit bonding of the strips to the bodyside liner and/or the containment flap material. In the machine direction 108, the position of the strips 118 can be registered relative to the absorbent assemblies 114 so that the product assemblage 113 can be cut between the absorbent assemblies with each strip 118 of side panel material 116 forming both a front side panel 34 and a back side panel 134 of consecutive pants.

One suitable applicator device 120 is disclosed in U.S. Pat. No. 5,104,116 issued Apr. 14, 1992 and U.S. Pat. No. 5,224,405 issued Jul. 6, 1993 both to Pohjola, which are incorporated herein by reference. The applicator device 120 can comprise a cutting assembly 122 and a rotatable transfer roll 124. The cutting assembly 122 employs a rotatable knife roll 126 and a rotatable vacuum anvil roll 128 to cut individual strips 118 from the continuous side panel material 116. The strips 118 cut by a blade on the knife roll 126 can be maintained on the anvil roll 128 by vacuum and transferred to the transfer roll 124.

The rotatable transfer roll 124 can comprise a plurality of rotatable vacuum pucks 130. The vacuum pucks 130 receive the strips 118 of material 116 from the cutting assembly 122 and rotate and transfer the strips to the continuously moving bodyside liner material 104. When the strips 118 are positioned as desired relative to the bodyside liner material 104, the strips are released from the pucks 130 by extinguishing the vacuum in the pucks. The pucks 130 can continue to rotate toward the cutting assembly 122 to receive other strips. As disclosed by Van Gompel et al., the material 116 used to form the side panels can alternatively be provided in continuous form and pressurized fluid-jets or a rotary die cutter can be employed to cut the material to form leg openings 52 of the undergarment. Still alternatively, the side panels 34, 134 of the training pants 20 can be provided by portions of the bodyside liner 42, outer cover 40 and/or other components of the pants.

A continuous supply of material 140 used to form the outer cover 40 can be provided from a supply roll 142 or other suitable source. The outer cover material 140 can be transported over a laminator roll 144 and banded to the bodyside liner material 104. The absorbent assemblies 114 are thereby sandwiched between the continuous materials 104 and 140. The inward portions of the strips 118 of side panel material 116 can also be disposed between the bodyside liner material 104 and the outer cover material 140. Alternative configurations for attaching the side panel material 116 are disclosed by Van Gompel et al. Various components such as leg elastics 58 or waist elastics 54 and 56 can be bonded to the outer cover material 140 at an application station 146 prior to uniting the bodyside liner and outer cover materials 104 and 140. Alternatively, leg elastics or waist elastics can be initially bonded to the bodyside liner material 104 or another material.

Bonding devices 148 such as ultrasonic bonders can be employed downstream from the laminator roll 144 to bond the bodyside liner material 104, side panel material 116 and outer cover material 140. For example, these materials can be transported between a rotary ultrasonic horn and an anvil roll. Suitable rotary ultrasonic horns are described in U.S. Pat. No. 5,110,403 to Ehlert, which is incorporated herein by reference. The bonding devices 148 could otherwise be a thermal, pressure or adhesive bonder as are well known.

The continuously moving product assemblage 113 next advances to a fastener application station 150 where fastening components 82, 84 are bonded to the strips 118 of side panel material 116. The location of the fastening components on the composite is a function in part of the configuration of the assembly system 100. As illustrated in FIG. 4, the assembly system 100 is configured so that the upward facing surface of the product assemblage 113 will become the outer surface 30 of the training pants 20 and the downward facing surface will become the inner surface 28. Moreover, the illustrated assembly system 100 is configured to produce partially assembled training pants having the front waist region 22 of a leading garment connected to the back waist region 24 of a trailing garment. However, it is understood that the assembly system 100 could alternatively employ any combination of different orientations. For example, the upward facing surface of the product assemblage 113 could form the inner surface 28 of finished garments. Additionally or alternatively, the back waist region 24 of a leading garment can be connected to the front waist region 22 of the trailing garment, or the garments can be arranged in a front-to-front/back-to-back relationship. Still alternatively, the assembly system 100 could be constructed as a cross-machine direction process wherein the longitudinal axis 48 of each garment could be perpendicular to the machine direction 108 during part or all of the assembly process.

Figure 5:
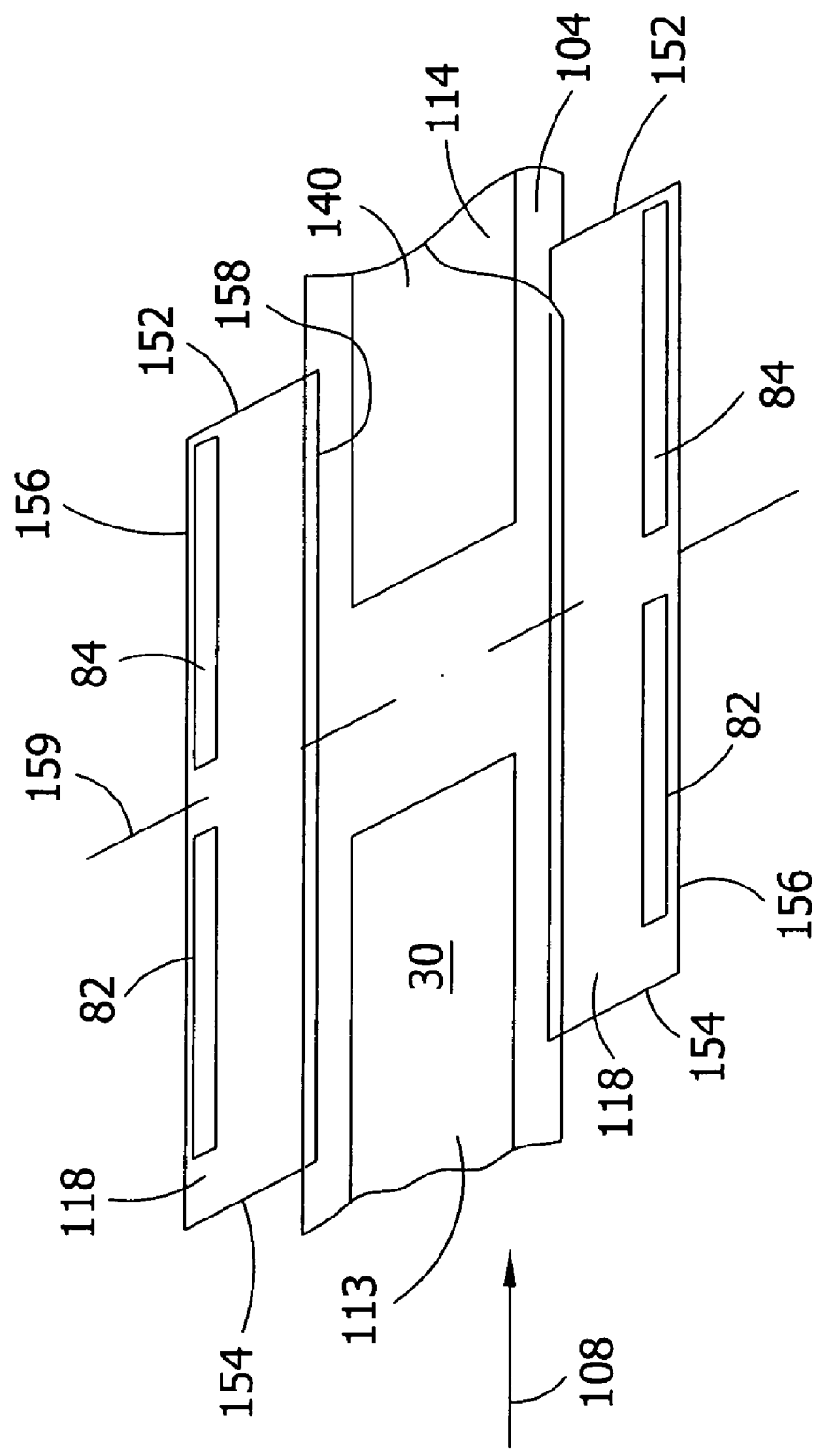
FIG. 5 is a schematic of a portion of a continuously moving assemblage or web of undergarments at one location along the assembly system of FIG. 4.

The locations of the fastening components 82, 84 in this embodiment are best illustrated in FIG. 5, which shows a portion of the product assemblage 113 moving in the direction of arrow 108 immediately following the fastener application station 150. Each individual strip 118 of side panel material 116 defines a leading edge 152, a trailing edge 154, a distal edge 156 and an interior edge 158. A dashed line 159 illustrates the location at which the product assemblage 113 can subsequently be cut to provide discrete partially assembled training pants. Based on the illustrated orientation of the continuously moving product assemblage 113, the first fastening components 82 can be bonded to the underside of the strips 118 and the second fastening components 84 can be bonded to the top of the strips. Additionally, the first fastening components 82 can be disposed relatively closer to the trailing edge 154 and the second fastening components 84 can be disposed relatively closer to the leading edge 152. The first fastening components 82 can be spaced in the machine direction 108 from the second fastening components 84 so that the cut line 159 passes therebetween.

With reference again to FIG. 4, continuous webs of a second fastener material 160 used to form the second fastening components 84 can be provided from supply rolls 162 or other suitable sources. The second fastener materials 160 can be cut into individual second fasteners 84 by cutting assemblies 164 or other suitable devices. The illustrated cutting assemblies 164 include rotatable knife rolls 166, rotatable vacuum anvil rolls 167, and rotatable backing rolls 168. The continuous second fastener materials 160 can be cut by blades on the knife rolls 166, maintained on the anvil rolls 167 by vacuum, and adhered on the top surfaces of the strips 118 of side panel material 116. Similarly, continuous webs of first fastener material 170 used to form the first fastening components 82 can be provided from supply rolls 172 or other suitable sources. The first fastener materials 170 can be cut into individual first fastening components by cutting assemblies 174 or other suitable devices. The illustrated cutting assemblies 174 include rotatable knife rolls 176, rotatable vacuum anvil rolls 177, and rotatable backing rolls 178. The continuous first fastener materials 170 can be cut by blades on the knife rolls 176, maintained on the anvil rolls 177 by vacuum, and adhered on the undersides of the strips 118 of side panel material 116.

It is contemplated that other arrangements can be used to attach the fastening components 82, 84 to the side panel material 116. For example, the fastening components 82, 84 can be applied to the side panel material 116 prior to uniting the side panel material with the bodyside liner material 104 and/or the outer cover material 140; the fastening components can be applied to the bodyside liner material 104 and/or outer cover material 140, whether separate side panels 34, 134 are used or not; portions of other components such as the bodyside liner and/or outer cover can form one or more of the fastening components; the separate side panels or integral side panels can themselves form one or more of the fastening components; the fastening components 82, 84 can be attached as pre-engaged composites or the like without departing from the scope of this invention.

After the fastening components 82, 84 are disposed on the strips 118 of side panel material 116, bonding devices 180 such as ultrasonic bonders, thermal bonders, pressure bonders, adhesive bonders or other suitable bonding devices can be employed to bond the fastening components to the strips. For example, the strips 118 can be transported between a rotary ultrasonic horn and an anvil roll, which devices are positioned on each side of the process at the cross machine direction location of the fastening components 82, 84. The strips 118 of side panel material 116 can be trimmed, for example, to provide angled and/or curved portions of the side panel material in the back waist region 24 (FIGS. 2 and 3). To this end, the assembly system 100 can include a die cutting roll 182 and a backing roll 184. In the illustrated embodiment, a portion of each strip 118 is trimmed from the trailing edge 154 (FIG. 7) in order to form the angled and/or curved portions in the back waist region 24.

Figure 6:
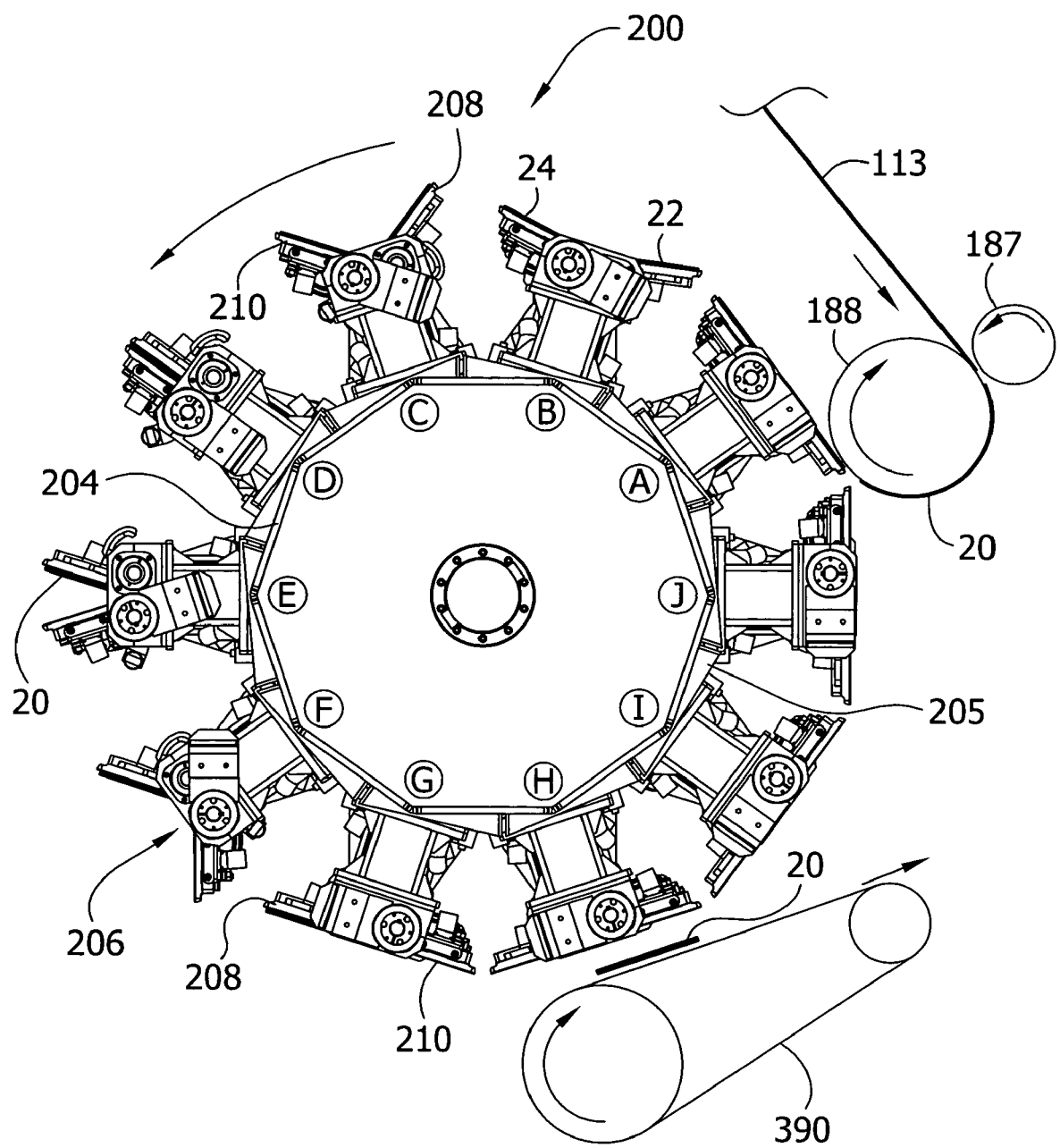
FIG. 6 is a schematic side elevation of one embodiment of fastening apparatus for folding and pre-fastening absorbent undergarments during the initial manufacture thereof.

With reference now to FIG. 6, the continuous assemblage 113 of partially assembled training pants 20 is fed through a nip formed between a cutting roll 187 and an anvil roll 188 to cut the web into discrete, partially assembled training pants 20 (broadly, undergarments). The cutting roll 187 can include one or more flexible hardened steel blades whereby the pinching force between the blade on the cutting roll 187 and the anvil roll 188 creates the cut. The cutting roll 187 can have one or more blades depending upon the desired distance between the cuts. The anvil roll 188 of the illustrated embodiment is suitably a vacuum anvil roll so that the discrete, partially assembled training pants are held by suction on the outer surface of the anvil roll after cutting.

FIG. 6 particularly illustrates one suitable embodiment of fastening apparatus, generally indicated at 200, for reconfiguring partially assembled absorbent undergarments to a folded and pre-fastened configuration in which the undergarments are fully assembled and ready to wear, such as in the manner of the training pants 20 of FIG. 1. The vacuum anvil roll 188 of the illustrated embodiment is suitably located adjacent the fastening apparatus 200 for transferring the discrete, partially assembled training pants directly to the apparatus in an unfastened and unfolded condition following cutting. It is understood, however, that the anvil roll 188 need not be a vacuum anvil roll and may be located distally from the fastening apparatus 200, with the discrete training pants 20 being delivered to the fastening apparatus by conveyor or other suitable transfer devices without departing from the scope of this invention. Broadly, then, the fastening apparatus 200 receives discrete, partially assembled absorbent undergarments (e.g., assembled but otherwise with the fastening components unfastened to each other and the garment unfolded) from a source of partially assembled absorbent garments. The source of partially assembled absorbent undergarments may comprise the assembly system 100 and cutting and anvil rolls 187, 188 described previously and illustrated in FIGS. 4 and 6, or another suitable assembly system and transfer device.

Moreover, in the illustrated embodiment the discrete training pants 20 are delivered in their longitudinal direction (e.g., parallel to longitudinal axis 48 of the pants) to the fastening apparatus 200, and in particular back edge 39 first with the outer cover 40 facing down against the fastening apparatus. However, it is understood that the discrete pants 20 may be delivered longitudinally to the fastening apparatus 200 front edge 38 first, or they may be delivered transversely (e.g., side edge 36 first) to the fastening apparatus 200, or they may be delivered to the fastening apparatus in a generally stacked arrangement and the entire undergarment overlaid onto the fastening apparatus at once without departing from the scope of this invention.

Figure 15:
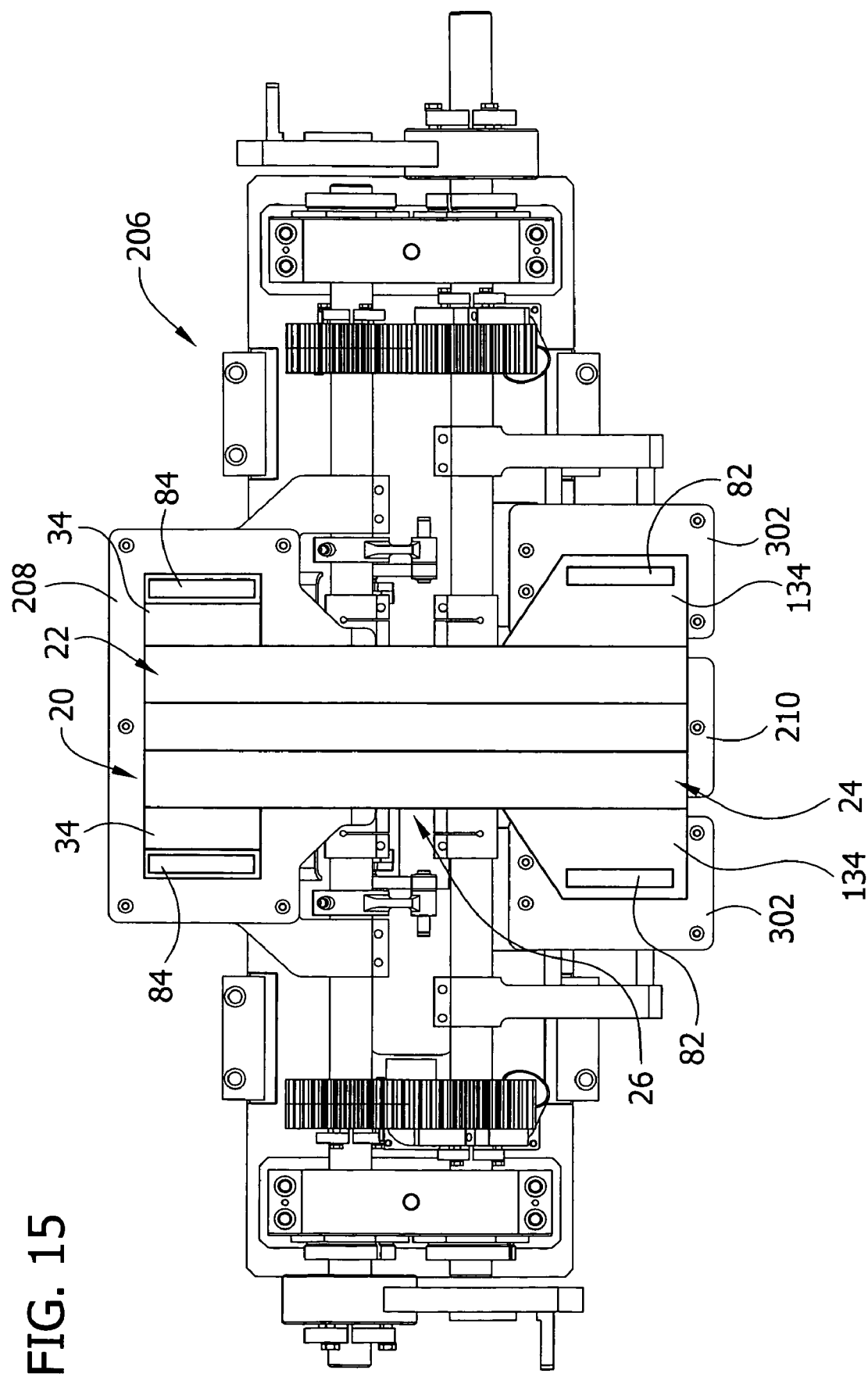
FIG. 15 is an end view of the folding device of FIG. 8, with the folding device in an open configuration and with an absorbent undergarment retained thereon for folding by the folding device.

In one particularly suitable embodiment, the discrete pants 20 may also be delivered to the fastening apparatus 200 with the front and back fastening portions (e.g., fastening components 82, 84) of the back and front side panels 134, 34 facing in the same direction, such as outward away from the fastening apparatus. For example, as illustrated in FIG. 15 the pants 20 may be configured with the front side panels 34 of the pants 20 folded transversely inward so that the fastening components 84 and the fastening components 82 face in the same direction. As a result, upon receipt by the fastening apparatus 200 of the partially assembled pants 20 in this configuration, both fastening components 82, 84 (i.e., broadly, the fastening portions at the front and back waist regions 22, 24) each face outward away from the fastening apparatus. It is understood that the fastening components 84 may be disposed on the opposite face of the side panels 34 so that the fastening portions (e.g., fastening components 82, 84) face in the same direction without transverse folding of the side panels.

Transverse folding of the front side panels 34 may suitably be performed before the assemblage 113 of partially assembled pants 20 is cut into discrete pants by the cutting roll 187, or it may be performed after cutting the assemblage into discrete pants but prior to the discrete pants being received by the fastening apparatus 200. It is understood, however, that the fastening portions (e.g., fastening components 84) at the front waist region 22 of the pants 20 may instead be folded transversely inward by the fastening apparatus 200 after delivery of the discrete pants to the fastening apparatus (i.e., while being carried by the fastening apparatus) without departing from the scope of this invention.

The fastening apparatus 200 of the illustrated embodiment comprises a drum (broadly, a transport device) 202 on which one or more of the discrete, partially assembled training pants 20 are carried during pre-fastening of the pants. The drum 200 is constructed of suitable frame structure 204 and paneling 205 and is operatively connected to suitable drive motor (not shown) for rotation on the axis of the drum to define a transport direction in which the drum (broadly, the transport device) moves as indicated by the direction arrow in FIG. 6. A plurality of longitudinal folding devices, generally indicated at 206, are carried by the drum 202 (e.g., ten such longitudinal folding devices are illustrated on the drum of FIG. 6) in the transport direction. The number of folding devices 206 may vary depending at least in part on the size of the drum, the size of the undergarment to be folded and pre-fastened, and the desired speed of the manufacturing line of which the fastening apparatus 200 is a part. As will be further discussed in detail herein, each folding device 206 is configured to receive the partially assembled training pants 20 and hold the training pants on the longitudinal folding device so that the drum, the longitudinal folding device and the training pants together move in the transport direction. The longitudinal folding device 206 is also operable to fold the training pants 20, e.g., with the front and back waist regions 22, 24 of the training pants in opposed relationship with each other, to facilitate fastening engagement between the fastening portions (e.g., fastening components 82, 84) of the pants as the folding device is moved in the transport direction.

Figure 10:
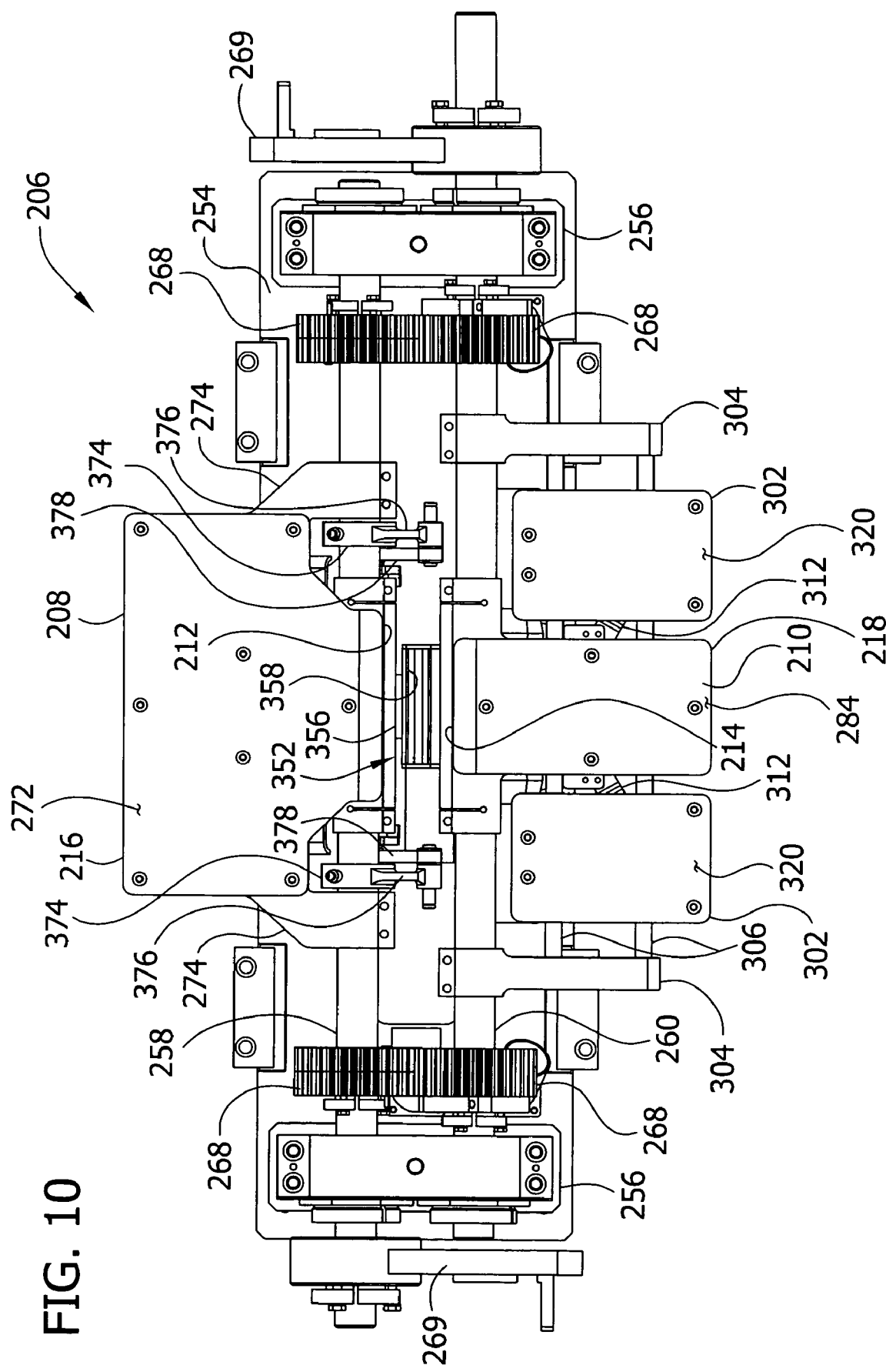
FIG. 10 is a top plan view of the folding device of FIG. 8.

Each longitudinal folding device 206 of the illustrated embodiment suitably comprises a pair of folding plates 208, 210 that are moveable relative to the drum 202 (i.e., the transport device) between an open configuration (e.g., as illustrated at angular positions A, G, H, I and J in FIG. 6) of the folding device in which the plates lie generally in the same plane as each other and are oriented generally tangentially relative to the drum and a closed configuration (e.g., as illustrated at angular position D in FIG. 6) of the folding device in which the plates are in opposed relationship with each other and oriented generally radially relative to the drum. The term longitudinal as used herein in reference to the folding device 206, and more particularly to the folding plates 208, 210, refers to the direction extending from inner ends 212, 214 (best illustrated in FIG. 14) of the folding plates to the opposite, or outer ends 216, 218 of the same respective folding plate. For example, in the open configuration of the longitudinal folding device 206 (FIG. 10) the longitudinal direction of each folding plate 208, 210 is tangential to the drum 202 and in the closed position of the folding device (FIGS. 6 and 18) the longitudinal direction of each folding plate is generally parallel to the radius of the drum.

Figure 14:
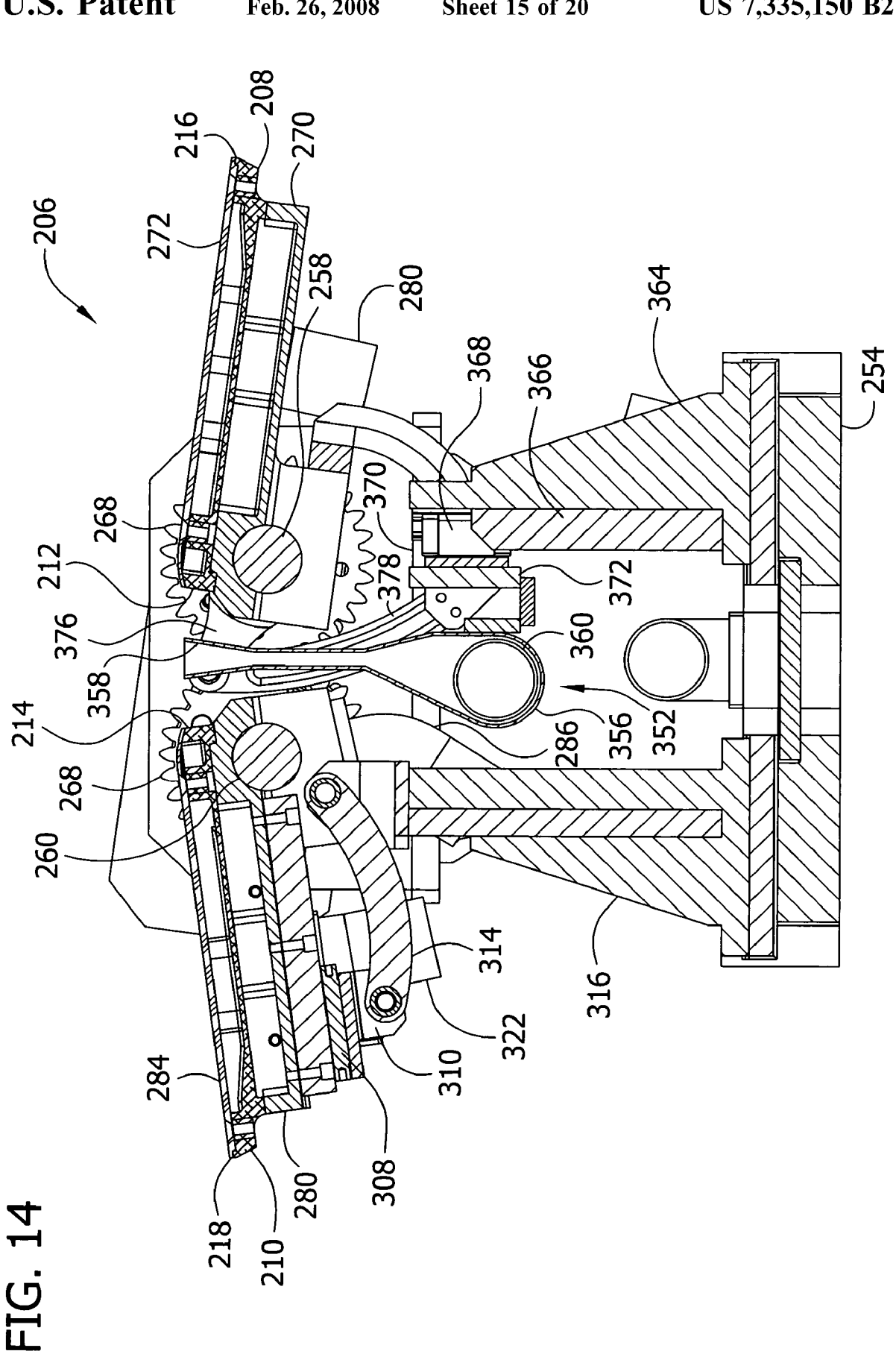
FIG. 14 is a cross-section taken in the plane of line 14-14 of FIG. 10.

The terms transverse and lateral as used herein in reference to the folding device 206 refer to the direction orthogonal to both the longitudinal direction of the plates 208, 210 and the radius of the drum 202, such as parallel to the rotation axis of the drum. The folding plates 208, 210 are suitably disposed adjacent the circumference of the drum 202 in the open configuration of the plates, and fold further outward away from the drum circumference in the closed configuration of the folding device 206. As best illustrated in FIG. 14, the inner ends 212, 214 of the folding plates 208, 210 are suitably spaced from each other.

One of the folding plates 208 (broadly, a first folding plate and otherwise referred to further herein as the front folding plate) is constructed to draw against and retain thereon at least the front waist region 22 of the pants 20 and the other folding plate 210 (broadly, a second folding plate and otherwise referred to further herein as the back folding plate) is constructued to draw against and retain thereon at least the back waist region 24 of the pants. In the illustrated embodiment of FIG. 6, the back folding plate 210 leads the front folding plate 208 as each folding device 206 moves in the transport direction (e.g., the direction in which the drum 202 rotates). It is understood, however, that the front folding plate 208 may instead lead the back folding plate 210 in the direction of movement of the drum 202 without departing from the scope of this invention.

Figure 7:
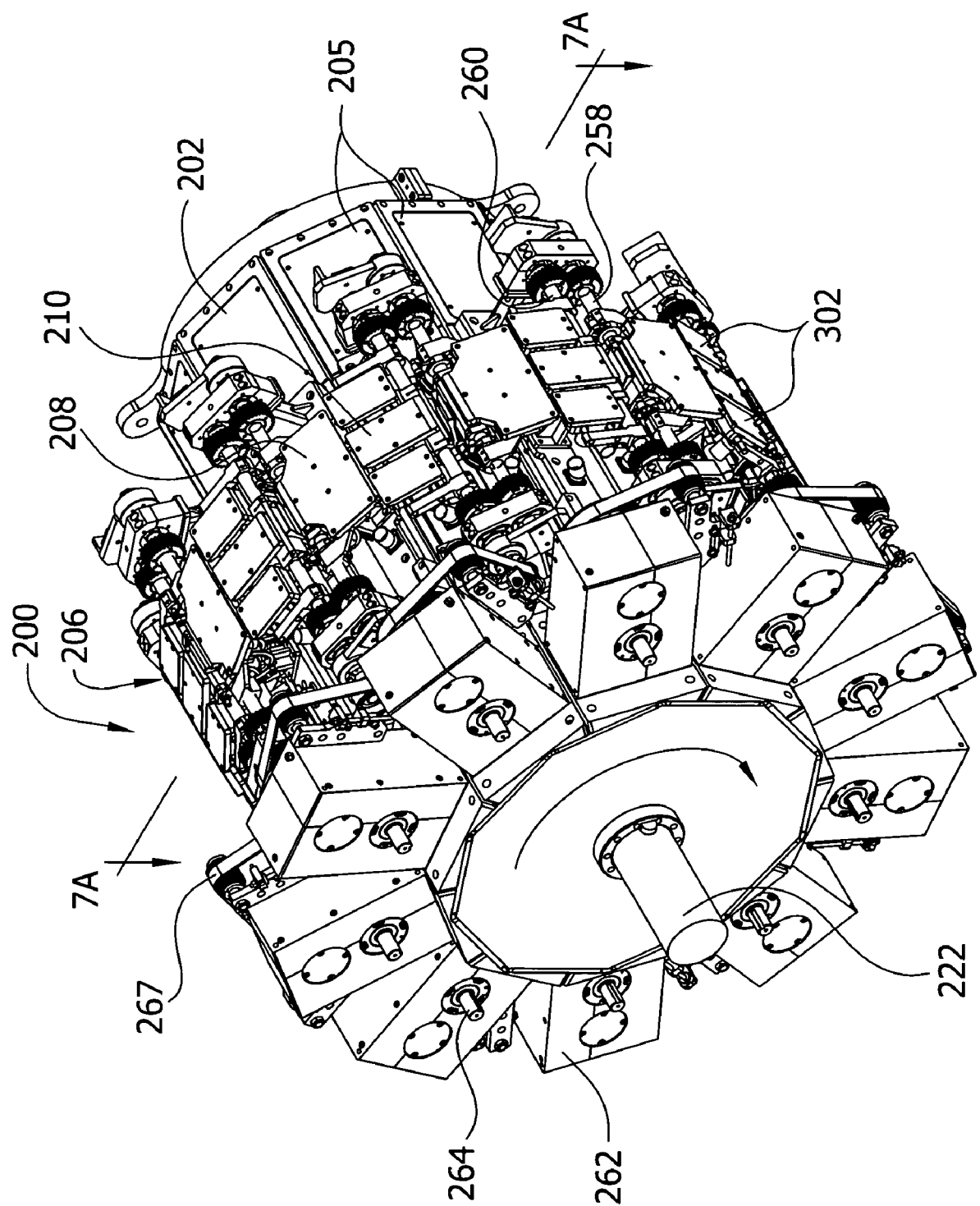
FIG. 7 is a perspective of the fastening apparatus of FIG. 6, with a drive system of the apparatus omitted.
Figure 7A:
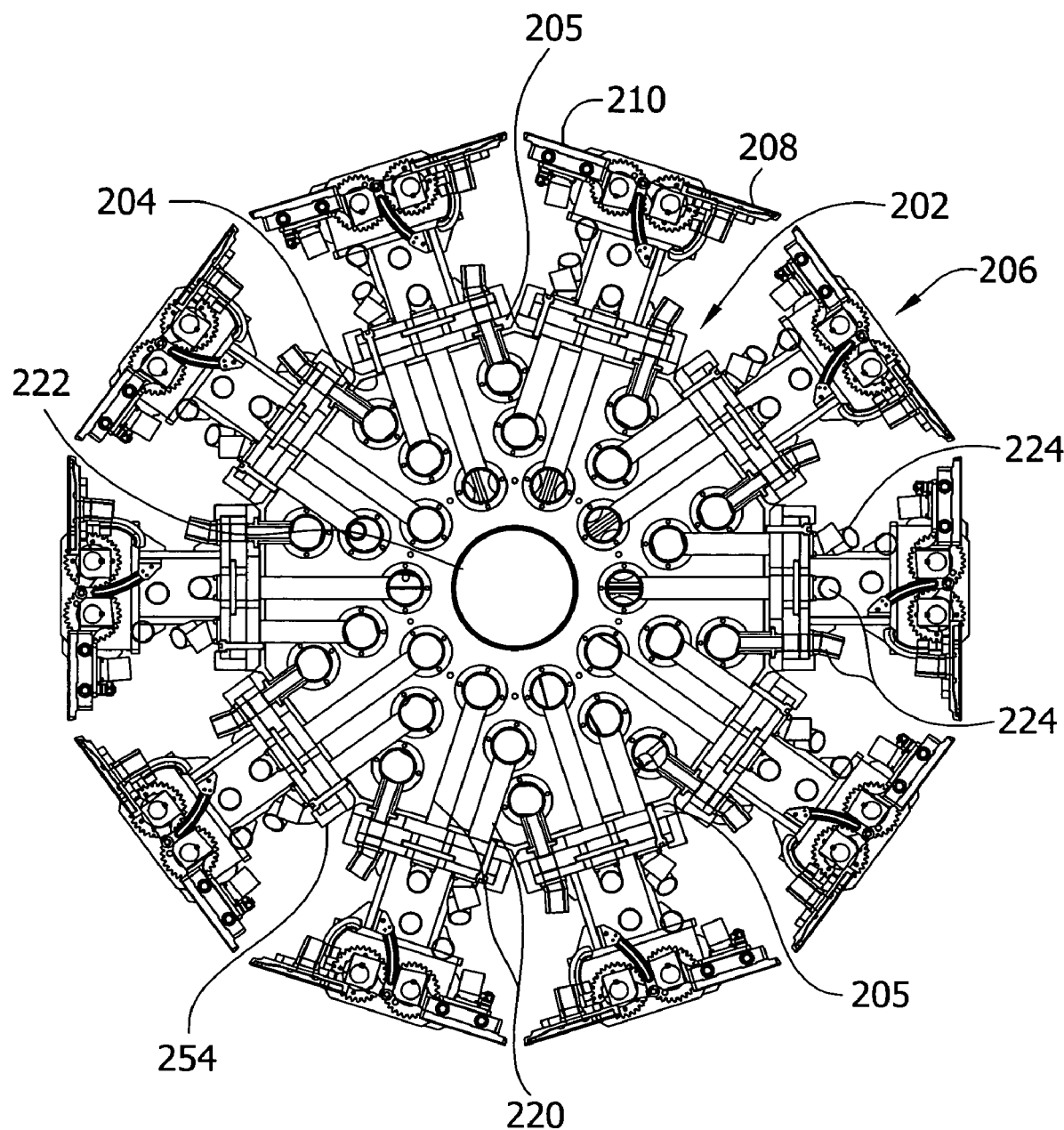
FIG. 7A is a cross-section taken in the plane of line 7A-7A of FIG. 7.

With particular reference to FIGS. 7 and 7A the interior of the drum 202 houses a plurality of vacuum lines 220, with various sets of the vacuum lines corresponding to each of the folding devices 206 and extending at one end to openings (not shown) in the respective panels 205 of the drum to which the folding devices are mounted in the manner described later herein. The opposite ends of the vacuum lines 220 are in fluid communication with a suitable vacuum shoe (not shown), which is in turn in fluid communication with a suitable vacuum source (not shown) operable to draw a vacuum on the various folding devices 206 via the vacuum shoe and vacuum lines. Vacuum shoes are well known in the art for controlling the delivery of vacuum pressure to multiple components of an apparatus such as the fastening apparatus 200 and thus the vacuum shoe is not described further herein except to the extent necessary to describe the present invention.

For purposes herein, the vacuum shoe is generally circular and has multiple rings of vents therein through which vacuum pressure is applied to the various vacuum lines 220 as the vacuum lines rotate with the drum on the rotation axis of the drum. Some of the vents are closed along certain arcuate segments of the vacuum shoe such that when the vacuum lines 220 for a particular folding device rotate past the closed vents, vacuum pressure to those vacuum lines is blocked. A suitable drive system (not shown) such as a drive motor (not shown) and one or more belts (not shown) drives rotation of central shaft 222 (FIG. 7) that is drivingly connected to the frame structure 204 of the drum 202. A stationary ring gear (not shown) having outward extending teeth about the circumference of the ring is fixed against rotation with the drum.

Figure 8:
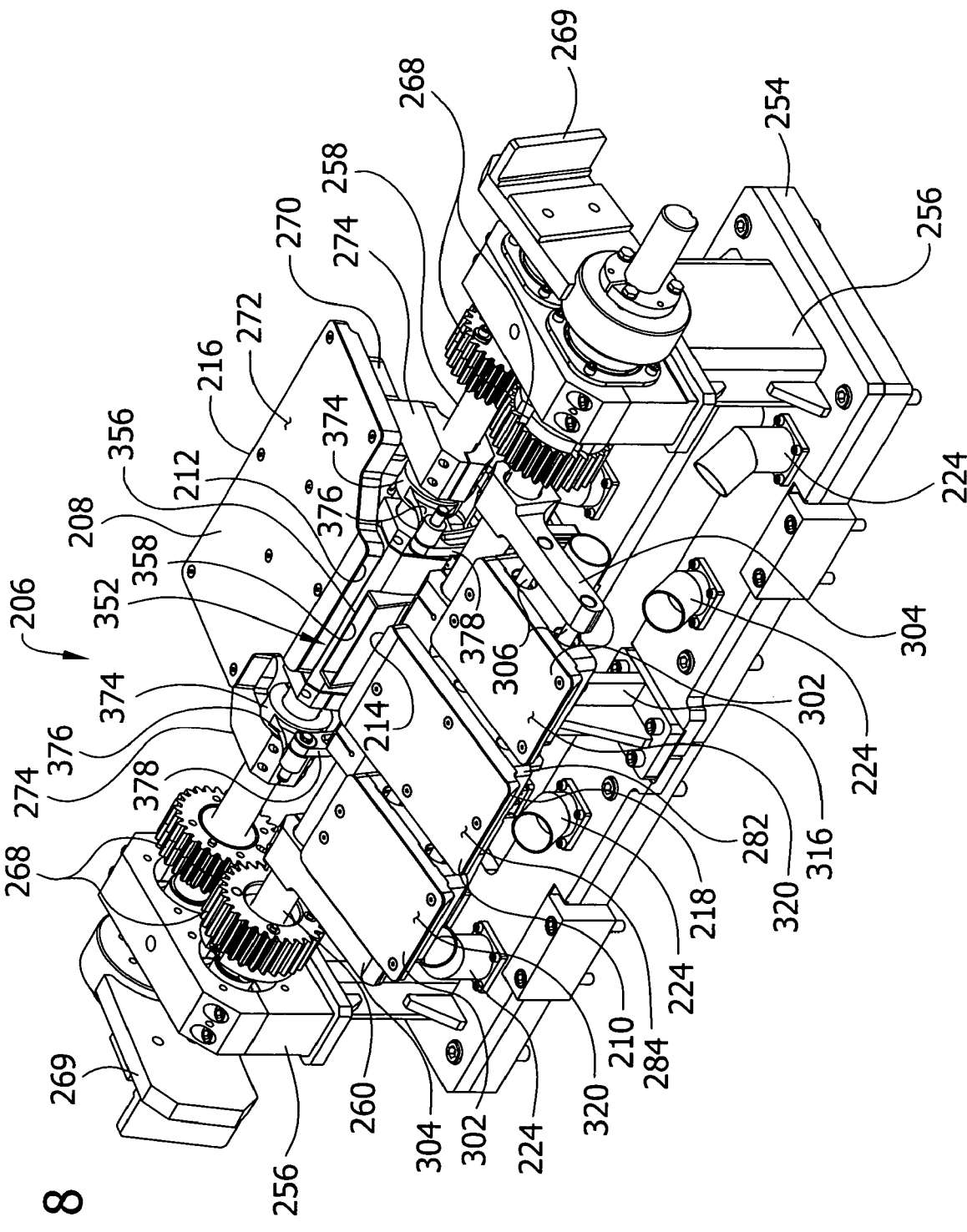
FIG. 8 is a perspective of a folding device of the folding apparatus of FIG. 6 as view from the top or outer side of the folding device, with vacuum hoses omitted.
Figure 9:
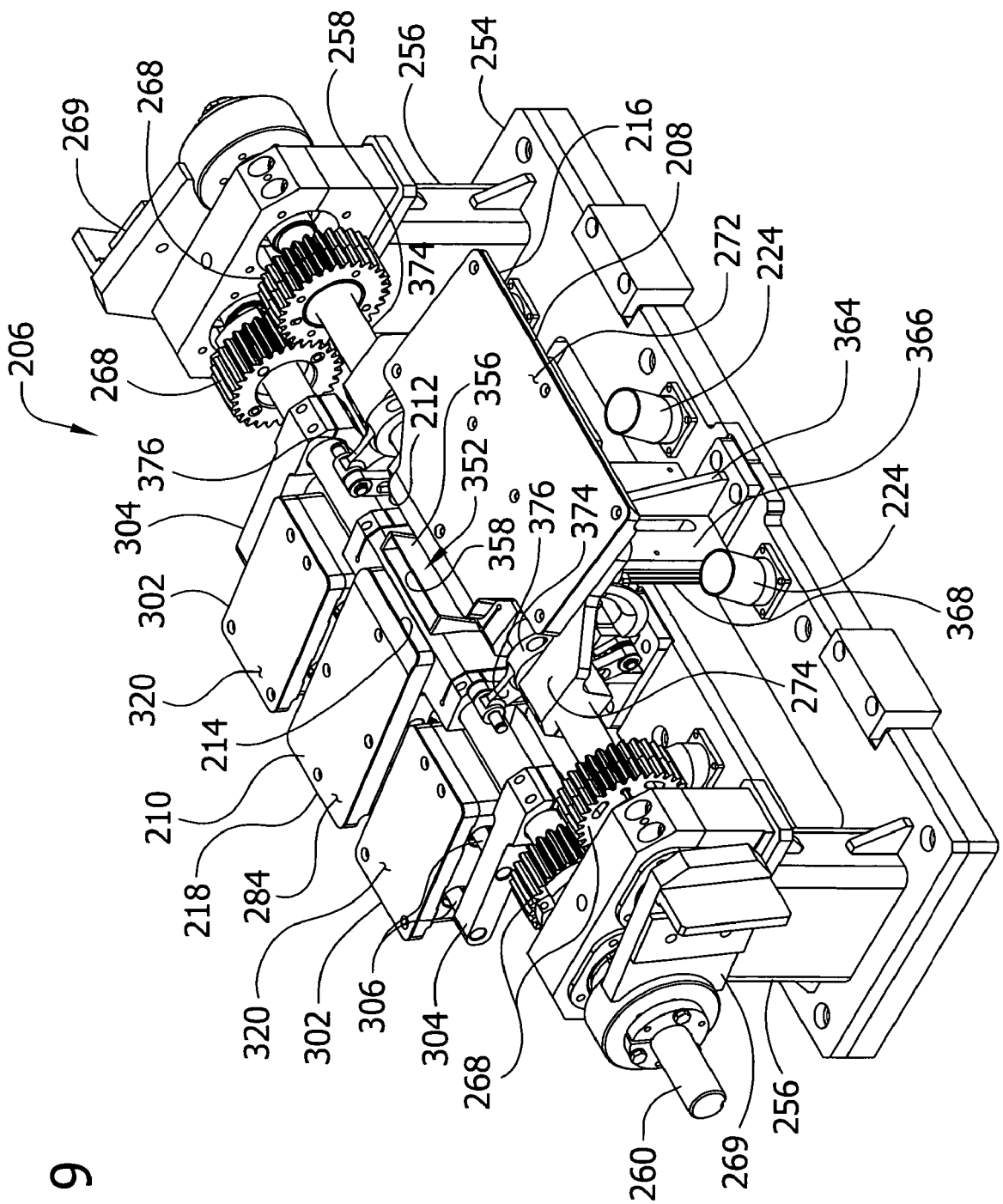
FIG. 9 is a another perspective of the folding device of FIG. 8.

FIGS. 8 and 9 illustrate one of the folding devices 206 and related components for folding and fastening one discrete pants 20 on the drum 202 as the drum rotates in the transport direction, it being understood that the other folding devices and related components mounted on the drum 202 are constructed and operate in substantially the same manner as the folding device and related components illustrated in FIGS. 8 and 9 and described further herein. A mounting plate 254 is suitably secured to the drum 202, with openings (not shown) formed in the mounting plate to permit fluid communication between the folding device 206 and the vacuum source of the fastening apparatus 200 via suitable connectors 224 (FIGS. 8 and 9), the openings (not shown) in the drum panel 205 (FIG. 7), and the vacuum lines 220 (FIG. 7A) housed within the drum 202. It is contemplated that a sealing gasket (not shown) may be provided between the mounting plate 254 and the drum 202 to seal the vacuum flow paths therebetween.

For reference purposes, the length of the mounting plate 254 is oriented to extend transversely on the drum 202 (transverse to the direction in which the drum rotates, i.e., parallel to the rotation axis of the drum). Still referring to FIGS. 8 and 9, a pair of shaft mounts 256 are secured to and extend outward from the mounting plate 254. A pair of bores are formed in each of the shaft mounts and have bearings seated therein to rotationally support a pair of shafts (designated herein as the front shaft 258 on which the front folding plate 208 is mounted and the back shaft 260 on which the back folding plate 210 is mounted) that extend between the shaft mounts.

The back shaft 260 extends outward of one of the shaft mounts 256 for driving connection to a suitable cam box 262 (FIG. 7). The cam box 262 is constructed to have a drive shaft 264 on which a planetary gear (not shown) is mounted for intermeshing with the large stationary ring gear of the fastening apparatus 200 such that upon rotation of the drum 202 on its rotation axis relative to the ring gear the planetary gear of the cam box 262 orbits the stationary ring gear and rotates the cam box drive shaft 264. A conventional cam box drive system 267 including suitable drive members and belts translates the drive shaft 264 rotation into driving movement of the back shaft 260 of the folding device 206 in a generally oscillatory rotation through an angle of approximately 90 degrees as illustrated in FIG. 6. That is, upon one 360 degree rotation of the drum 202 relative to the ring ring, the back shaft 260 of the folding device 206 rotates from an initial angular position corresponding to the open configuration of the folding device to an angular position 90 degrees relative thereto corresponding to the closed configuration of the folding device and then back to its initial angular position.

Suitable intermeshing gears 268 drivingly connect the back shaft 260 to the front shaft 258 in counter-rotating relationship whereby rotation of the back shaft in one direction drives rotation of the front shaft in the counter direction. It is understood that the back shaft 260 and front shaft 258 may be rotated through a rotation angle of less than or greater than 90 degrees without departing from the scope of this invention. Counterweights 269 are also mounted on one end of each of the front and back shafts 258, 260 as illustrated in FIG. 7.

Figure 11:
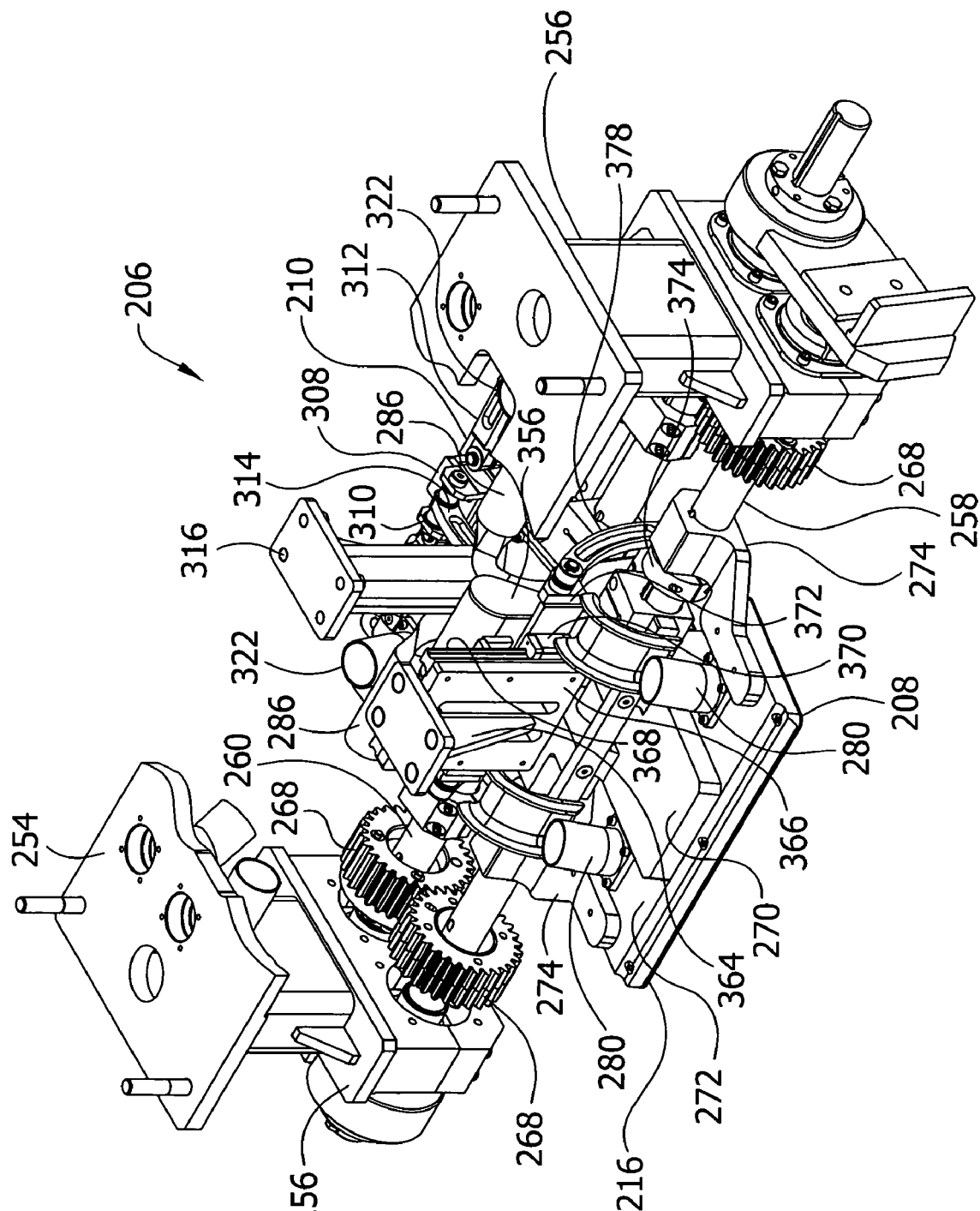
FIG. 11 is a perspective of the folding device of FIG. 8 as viewed from the bottom or inner side of the folding device, with vacuum hoses omitted and with portions broken away to reveal additional construction.

With particular reference to FIGS. 9 and 11, the front folding plate 208 suitably comprises a back panel 270 fixedly mounted on the front shaft 258 for conjoint rotation therewith and a porous cover panel 272 secured to the back panel. The back panel 270 is suitably configured so as to together with the cover panel 272 form an interior chamber of the front folding plate. Additional support members 274 are fixedly mounted on the front shaft 258 in spaced relationship with each other and further support the transverse side margins of the cover panel 272. The cover panel 272 for the front folding plate 208 has a width (i.e., transverse dimension) such that the folding plate extends transversely up to and more suitably transversely outward beyond the front fastening portions (e.g., the folded fastening components 84 in the illustrated embodiment) of the pants 20.

Vacuum inlets (not shown) in the back panel 270 provide for fluid communication of the interior chamber of the front folding plate 208 with the vacuum source via suitable connectors (not shown), vacuum hoses (not shown) between the connectors and the vacuum inlets, the vacuum connectors 224 on the mounting plate, the vacuum lines 220 within the drum, and the vacuum shoe. Accordingly, the front folding plate 208 is operable in a vacuum mode in which a vacuum is drawn on the porous cover panel 272 to draw and retain the front waist region 22 of the pants 20 against the surface of the cover panel. Additional connectors 280 and vacuum hoses (not shown) are connected to the back side of the cover panel 272 transversely outward of the back panel 270 to draw a vacuum on the outer side margins of the cover panel in the vacuum mode of the front folding plate 208 to draw and retain the front fastening portions (e.g., the folded fastening components 84 in the illustrated embodiment) of the pants 20 on the cover panel of the front folding plate.

Figure 12:
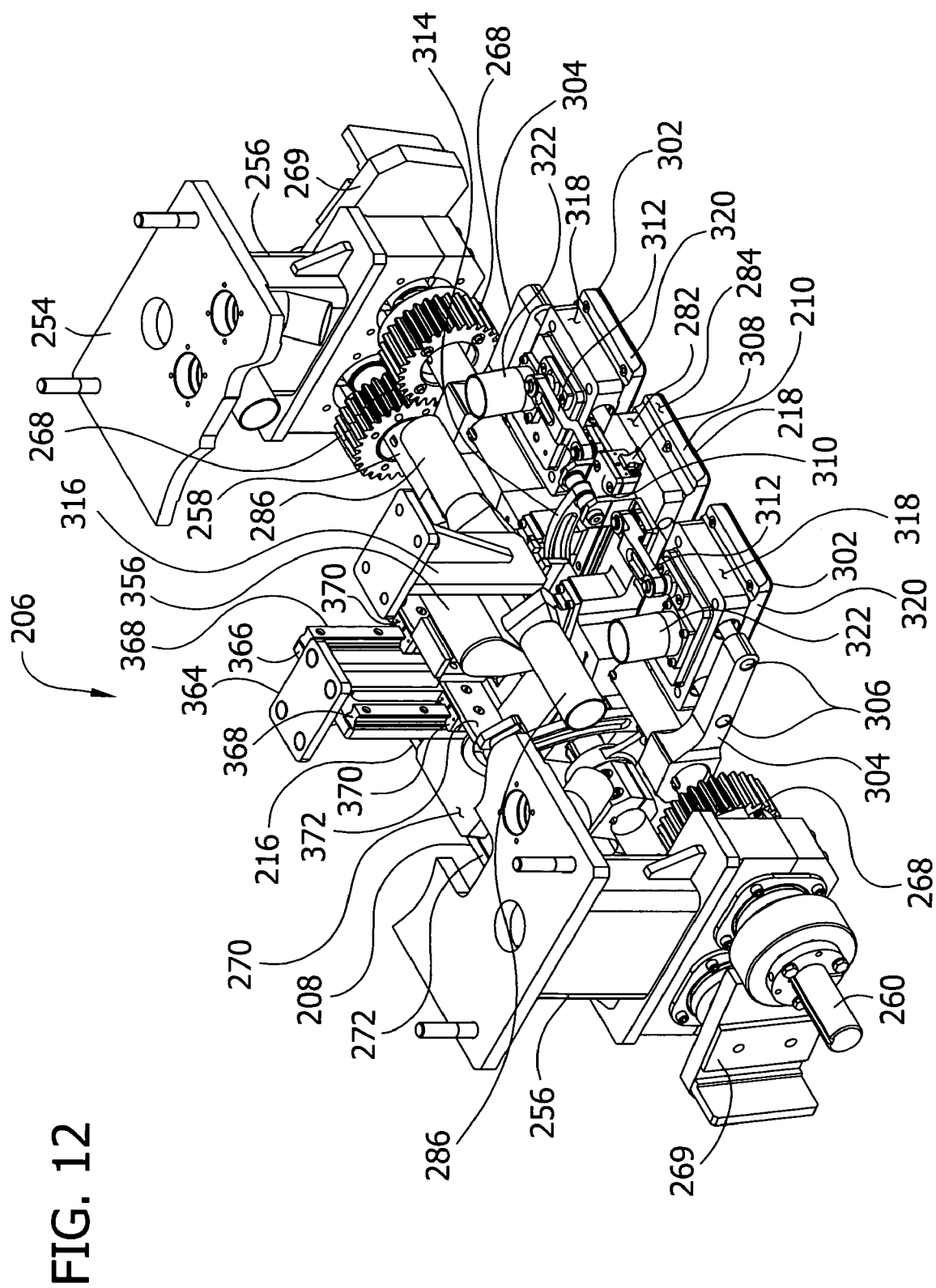
FIG. 12 is another perspective similar to FIG. 11.

The back folding plate 210, with reference to FIGS. 8 and 12, suitably comprises a back panel 282 fixedly mounted on the back shaft 260 for conjoint rotation therewith, and a porous cover panel 284 secured to the back panel. The back panel 282 is suitably configured so as to together with the cover panel 284 form an interior chamber of the front folding plate. The cover panel 284 for the back folding plate 210 is suitably sized in width (e.g., in transverse dimension) smaller than the cover panel 272 of the front folding plate 208. For example the cover panel 284 of the back folding plate 210 may have a width such that the cover panel extends transversely inward of or adjacent to the side panels 134 at the back waist region 24 of the pants 20, and in other embodiments it may extend transversely outward of a portion of each side panel 134 as long as it terminates transversely inward of the back fastening portions (e.g., the fastening components 82 in the illustrated embodiment) of the pants 20.

Vacuum inlets (not shown) in the back panel 282 provide for fluid communication of the interior chamber of the back folding plate 210 with the vacuum source of the fastening apparatus 200 via suitable connectors 286, vacuum hoses (not shown), the connectors 224 on the mounting plate 254, the vacuum lines 220 within the drum 202 and the vacuum shoe described previously. Accordingly, the back folding plate 210 is operable in a vacuum mode in which a vacuum is drawn on the porous cover panel 284 to draw and retain the back waist region 24 of the pants 20 against the surface of the cover panel.

To facilitate proper alignment of the back fastening portions (e.g., fastening components 82) of the back waist region 24 of the pants 20 with the front fastening portions (e.g., the folded fastening components 84) of the front waist region 22 of the pants, a pair of transverse retention plates (broadly, transverse retention members), generally indicated at 302, are provided generally transversely adjacent to and on opposite sides of the back folding plate 210 and are moveable transversely relative to the back folding plate. In the illustrated embodiment, the transverse retention plates 302 are suitably connected to the back folding plate 210 for conjoint movement with the back folding plate between the open and closed configurations of the folding device 206. More particularly, a pair of transversely spaced support arms 304 are mounted on the back shaft 260 for conjoint rotation therewith and support a pair of transversely extending cross-bars 306 that extend through the back folding plate. The transverse retention plates 302 are each slidably mounted on the cross-bars 306 to permit transverse sliding movement of the retention plates relative to the back folding plate 210 (as well as relative to the front folding plate 208) while moving conjointly with the back folding plate between the open and closed configurations of the folding device 206.

In one particularly suitable embodiment, the transverse retention plates 302 are operatively connected to the back folding plate 210 such that the retention plates are responsive to movement of the back folding plate between the open and closed configurations of the folding device 206 to move transversely relative to the back folding plate. For example, in the illustrated embodiment a longitudinal rail 308 (FIG. 12) is mounted on the back panel 282 of the back folding plate 210. A suitable slide 310 is mounted on the rail 308 for longitudinal sliding movement on the rail. A pair of transverse links 312 are each pivotally connected at one end to the slide 310 and pivotally connected at their opposite end to a respective one of the transverse retention plates 302. Accordingly, movement of the slide 310 longitudinally along the rail 308 causes the transverse links 312 to pull or push the transverse retention plates 302 inward or outward relative to the back folding plate 210.

To couple this motion to the folding movement of the back folding plate 210, a separate longitudinally extending link 314 is pivotally connected at one end to the slide 310 and is pivotally connected at its other end to a stationary upright 316 that is fixed to the mounting plate 254. The length of the longitudinal link 314 is such that in the open position of the folding device 206 the slide 310 is generally adjacent the outer end 218 of the back folding plate 210. Upon rotation of the back shaft 260 and back folding plate 210 toward the closed position of the folding device 206, the slide is pulled by the link 314 to ride down along the rail 308 toward the inner end 212 of the back folding plate 210. Accordingly, as the slide 310 rides down along the rail 308, the transverse retention plates 302 are pulled by the transverse links 312 transversely inward relative to the back folding plate 210. In like manner, rotation of the back folding plate 210 back toward the open configuration of the folding device 206 causes the transverse links 312 to push the transverse retention plates 302 transversely outward relative to the back folding plate.

As illustrated in FIGS. 8, 12 and 14, each of the transverse retention plates 302 comprises a back panel 318 and corresponding cover panel 320 that together define an interior chamber of each respective retention plate. The interior chambers of the transverse retention plates 302 are in fluid communication with the vacuum source via suitable connectors 322, vacuum hoses (not shown), the vacuum connectors 224 on the mounting plate 254, the vacuum lines 220 within the drum 202 and the vacuum shoe described previously for operation of the retention plates in a vacuum mode in which the back fastening portions (e.g., in the illustrated embodiment, the fastening components 82) of the pants are drawn against and retained on the retention plates for transverse movement with the retention plates.

In the illustrated embodiment, the cover panels 320 of the transverse retention plates 302 are generally flat so as to be generally planar with the cover panel 284 of the back folding plate 210. However, it is understood that the cover panels 320 of the retention plates 302 need not be planar with the cover panel 284 of the back folding plate 201. For example, the cover panels 320 of the retention plates 302 may be configured to extend further inward toward the front folding plate 208 than the back folding plate 210 in the closed configuration of the folding device 206 to facilitate engagement of the front and back fastening portions (e.g., fastening components 84, 82 in the illustrated embodiment).

It is also understood that the cover panels 320 of the retention plates 302 need not be flat so as to extend nearer to the front folding plate 208 than does the back folding plate 210 in the closed configuration of the folding device 206. It is further understood that transverse movement of the retention plates 302 need not be coupled to folding movement of the back folding plate 210. Additionally, the transverse movement of the retention plate relative to the back folding plate 210 may be achieved by suitable construction other than as illustrated and described herein without departing from the scope of this invention.

While in the illustrated embodiment the front and back folding plates 208, 210 use vacuum to retain the front and back waist regions 22, 24 of the pants 20 thereon during folding, it is understood that the front and back waist regions of the pants may be retained on one or both of the front and back folding plates other than by vacuum, such as by friction, adhesive, clips or other suitable means without departing from the scope of this invention. It is also understood that the tranverse retention members 302 may be configured to retain the fastening portions (e.g., fastening components 82) thereon other than by vacuum and remain within the scope of this invention.

Figure 13:
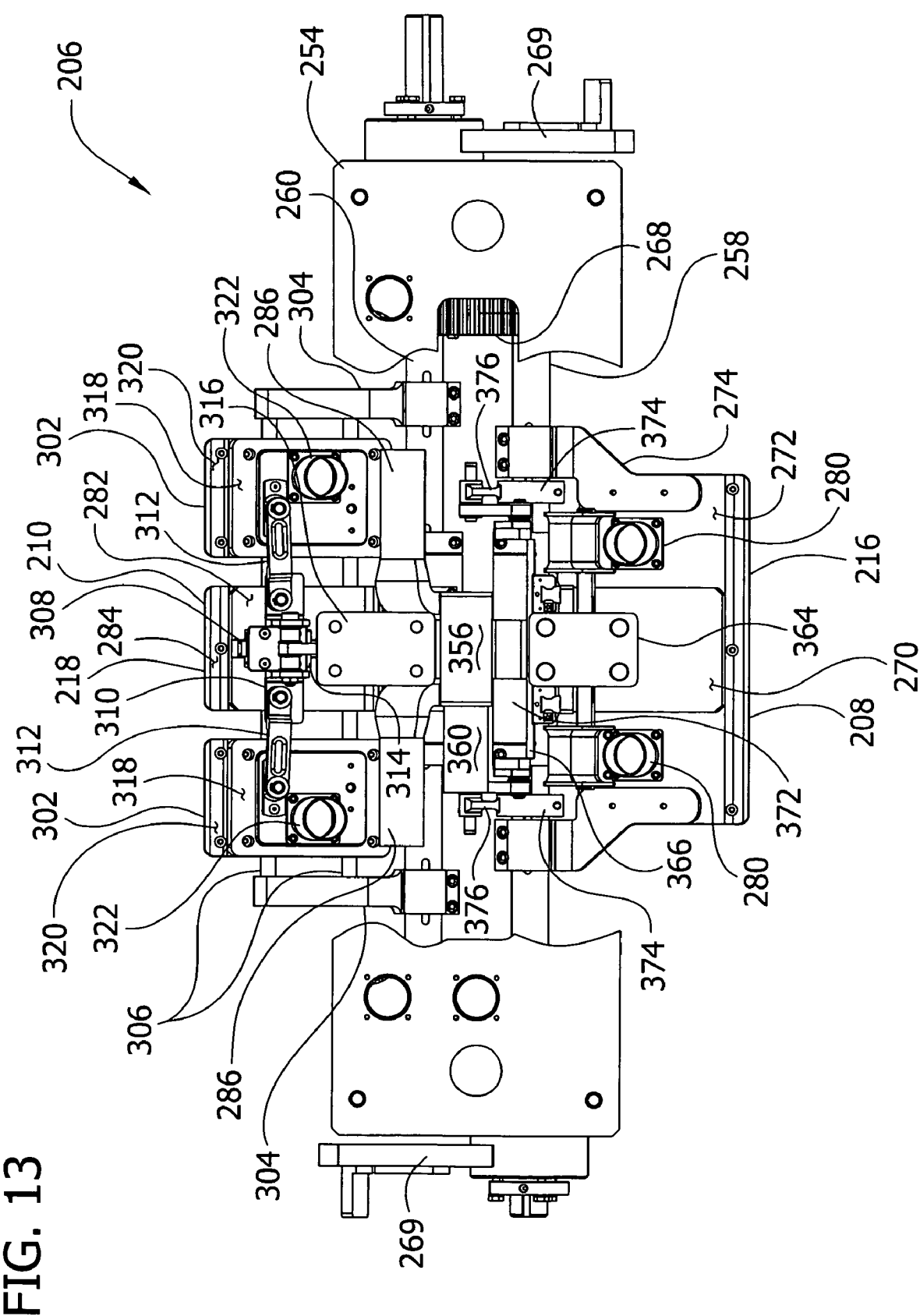
FIG. 13 is a bottom plan view of the folding device of FIG. 8 with portions broken away to reveal additional construction.
Figure 19:
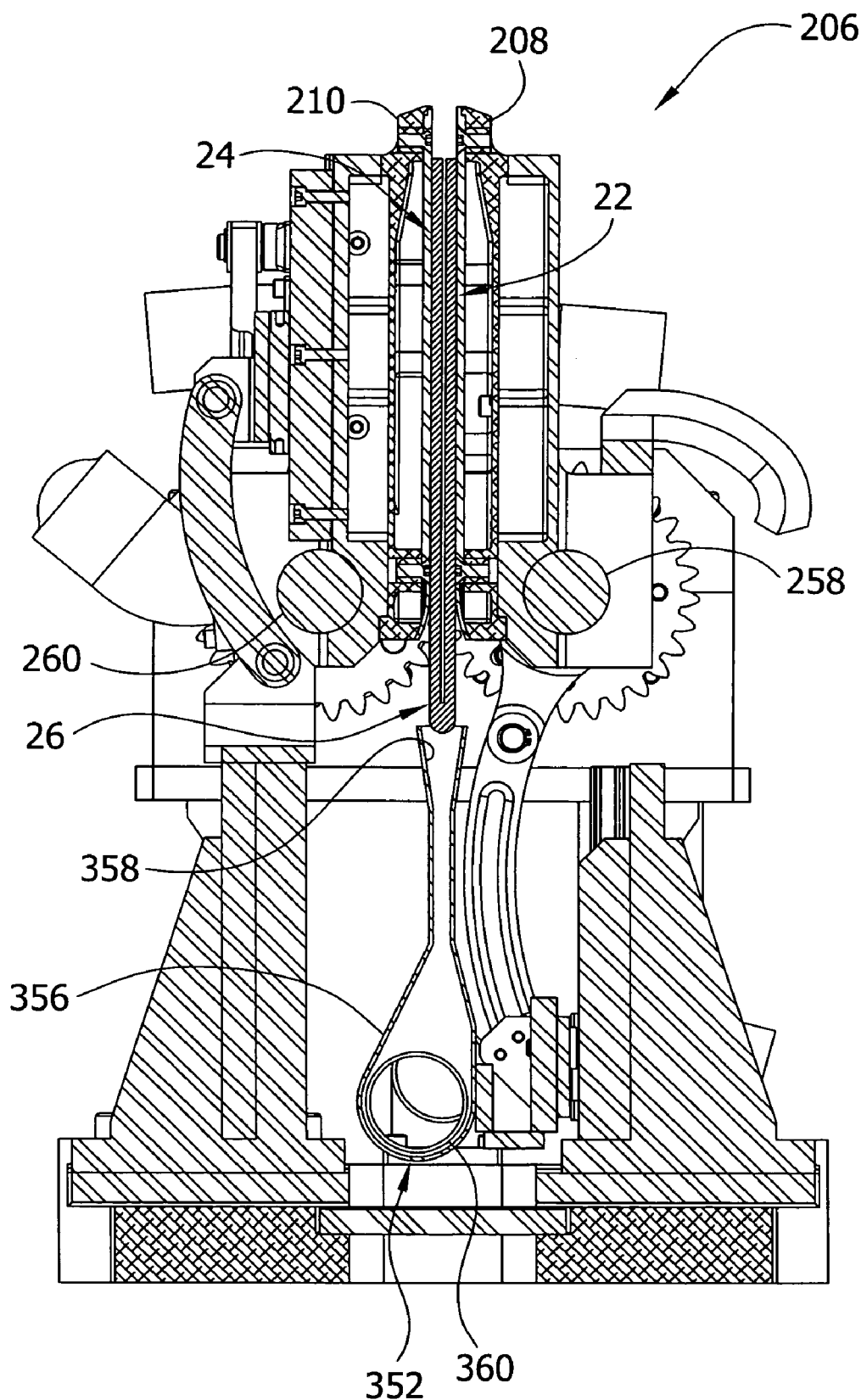
FIG. 19 is a cross-section similar to that of FIG. 14 but with the folding device in its closed configuration and illustrating an absorbent undergarment folded and pre-fastened by the folding device.

Upon folding of the pants 20 by the folding device 206, there is a tendency for the portion of the central or crotch regions 26 of the pants (e.g., due to the leg and flap elastics) to want to ride up between the folding plates 208, 210, which may negatively effect the folding of the plates and/or the pants. Referring particularly now to FIGS. 9, 13 and 14, a holding device, generally indicated at 352, is therefore disposed intermediate the inner ends 212, 214 of the front and back folding plates 208, 210 to position the central or crotch region 26 of the pants 20 that longitudinally spans the inner ends of the folding plates outward of the inner ends of the folding plates at least in the closed configuration of the folding device as illustrated in FIG. 19 and more suitably as the folding plates are moved from the open configuration to the closed configuration of the folding device 206. That is, the holding device 352 suitably holds the central, or crotch region 26 of the pants 20 during folding of the pants by the folding device 206 to inhibit the crotch region of the pants against bunching or moving up between the folding plates 208, 210 during folding of the pants.

The illustrated holding device 352 suitably comprises a suction device including a vacuum duct 356 having an elongate inlet 358 that extends transversely between the inner ends 212, 214 of the folding plates 208, 210. The vacuum duct 356 is in fluid communication with the vacuum source, such as via a suitable connector 360 (FIG. 14), vacuum hoses (not shown), the vacuum connectors 224 on the mounting plate 254, the vacuum lines 220 within the drum 202 and the vacuum shoe, for operation of the suction device in a vacuum mode in which the suction device draws the crotch or central region 26 of the pants 20 toward the inlet 358 of the suction device 352. It is understood that the holding device 352 may comprise other than a suction device, such as a blower device that blows pressurized air against the inner surface of the central region 26 of the pants 20 between the inner ends 212, 214 of the folding plates 208, 210, or any suitable mechanical holding device that physical contacts and grips or otherwise holds the central region 26 of the pants during folding of the pants by the folding plates.

In one particularly suitable embodiment the holding device 352 (e.g., the suction device in the illustrated embodiment) is moveable relative to the front and back folding plates 208, 210, such as in a radial direction, i.e., inward and outward, relative to the drum 202. More suitably, the holding device 352 is operatively connected to one of the front and back folding plates 208, 210 (e.g., the front folding plate in the illustrated embodiment) such that movement of the folding plates between the open and closed configurations of the folding device 206 operates to move the holding device relative to the folding plates (i.e., the holding device movement is responsive to movement of the folding plates).

As illustrated in FIGS. 12 and 14, an upright 364 is fixedly secured to the mounting plate 254 generally adjacent the front shaft 258 and a rail panel 366 is formed integrally with the upright, with the rail panel facing the holding device 352. A pair of rails 368 are mounted longitudinally on the rail panel 366 in transversely spaced relationship with each other and suitable slides 370 ride respectively on the rails. A mounting frame 372 transversely spans the rails 368 and is connected to the slides 370 for conjoint movement with the slides. The holding device 352, e.g., the suction device and more particularly the vacuum duct 356, is secured to the mounting frame 372 for sliding movement with the slides 370 relative to the rail panel 366.

To couple movement of the holding device 352 with folding movement of the front folding plate 208, a pair of collars 374 are mounted on the front shaft 258 for conjoint rotation with the shaft. A lever arm 376 is formed integrally with each of the collars 374 and is pivotally connected at its free end to a respective link 378. The links 378 are each pivotally connected at their opposite ends to the mounting frame 372 to which the holding device 352 is secured. In the illustrated embodiment the links 378 are sized such that in the open configuration of the folding device 206 the slides 370 are near the front shaft 258. Upon rotation of the front shaft 258, and hence folding of the front folding plate 208 toward the closed configuration of the folding device 206, the mounting frame 372 and slides 370 are pulled by the links 378 down along the rails 368 to conjointly move the holding device 352 downward (e.g., radially inward) relative to the folding plates 208, 210 and the drum 202.

It is understood that the holding device 352 may suitably be moveable relative to the folding plates 208, 210 other than by being operatively connected to one of the folding plates. It is also understood that the holding device 352 may remain stationary relative to the folding plates 208, 210 upon movement of the folding plates between the open and closed configurations of the folding device 206 without departing from the scope of this invention.

In operation according to one embodiment of a method for mechanically forming a pre-fastened absorbent undergarment, discrete partially assembled undergarments (e.g., training pants 20) are delivered sequentially from the source of partially assembled undergarments (e.g., from the assembly system 100, cutting roll 187 and vacuum anvil roll 188 in the illustrated embodiments of FIGS. 4 and 6) to the fastening apparatus 200 generally unfolded (longitudinally) and unfastened. The fastening portions (e.g., fastening components 84) of the front waist region 22, and more particularly the front side panels 34 in the illustrated embodiment are folded transversely prior to delivery of the pants 20 to the fastening apparatus 200 so that the fastening portions of the front side panels face outward away from the fastening apparatus. The drum 202 of the fastening apparatus 200 is continuously driven to rotate on its axis so that the multiple longitudinal folding devices 206 on the drum sequentially pass by the vacuum anvil roll 188 to receive the training pants 20 onto the folding devices. At the angular position of the drum 202 identified as angular position A in FIG. 6, the longitudinal folding plates 208, 210 of one longitudinal folding device 206 have just passed the vacuum anvil roll 188 with the folding device 206 in its open configuration, i.e., with the folding plates spread apart and in generally planar relationship with each other tangential to the drum 202.

A discrete, partially assembled pair of training pants 20 has been received by the longitudinal folding plates 208, 210 with the folding plates and transverse retention plates 302 operating in their respective vacuum mode to draw and retain the training pants 20 on the folding plates and retention plates. In particular, as illustrated in FIG. 15, the front waist region 22 and corresponding folded fastening portions (e.g., the fastening components 84) are drawn against and retained on the cover panel 272 of the front folding plate 208. At least a portion of the back waist region 24 of the training pants 20 is drawn against and retained on the cover panel 284 of the back folding plate 210 and the back side panels 134 and more suitably the fastening portions (e.g., fastening components 82 in the illustrated embodiment) are drawn against and retained on the transverse retention plates 302. The holding device 352, e.g., the suction device disposed between the inner ends 212, 214 of the folding plates 208, 210, is operated in its vacuum mode to draw the center region (e.g., crotch region 26) of the pants 20 toward the inlet 358 of the duct 356. At this stage, the fastening portions associated with the back side panels 134 of the pants 20 are out of transverse alignment with the fastening portions associated with the front side panels 34 of the pants.

Figure 16:
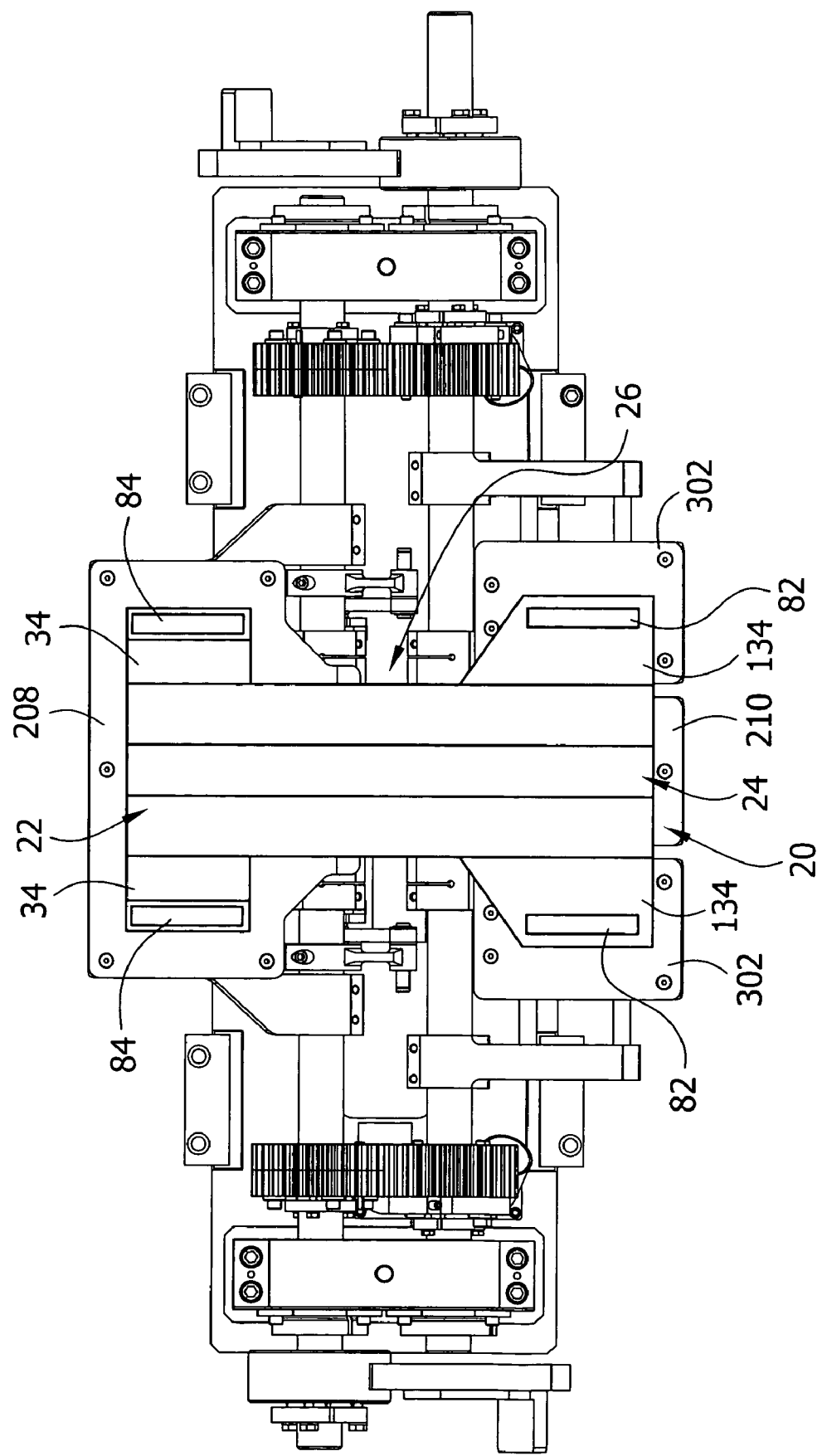
FIG. 16 is an end view similar to that of FIG. 15 with the folding device moved further towards a closed configuration of the folding device.
Figure 17:
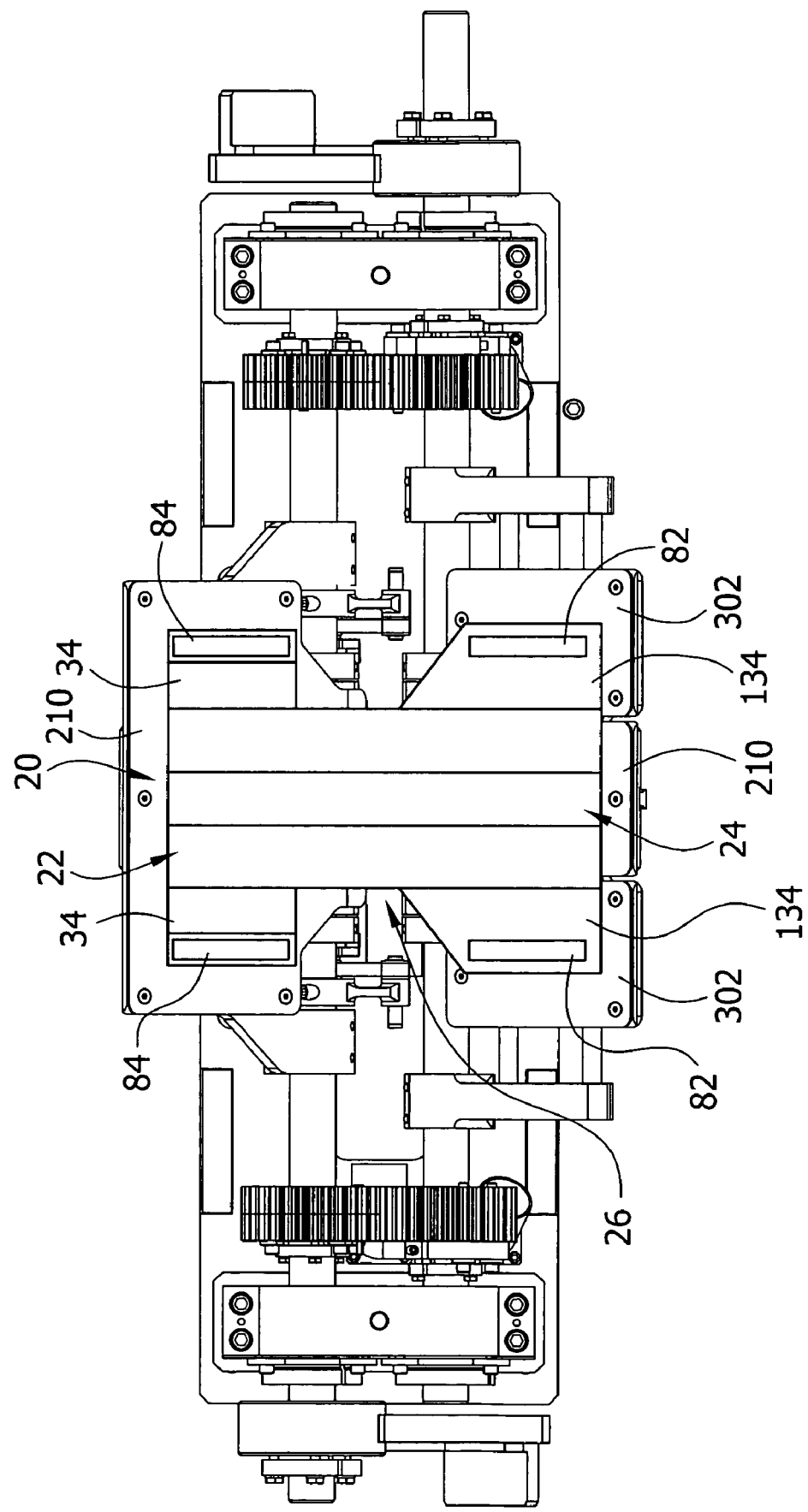
FIG. 17 is an end view similar to that of FIG. 16 with the folding device moved even further towards the closed configuration of the folding device.

As the drum 202 further carries the training pants 20 in the transport direction (e.g., the counter-clockwise direction in the illustrated embodiment) to the angular position indicated in FIG. 6 as position B, the cam box planetary gear 266 orbits the stationary ring gear, driving rotation of the planetary gear and corresponding cam box drive shaft 264 on which the cam box gear is mounted. The back shaft 260 of the folding device 206 caused to rotate by the cam box, which via the gears 268 on the front and back shafts 258, 260 of the folding device drives concurrent rotation of the front shaft, to initiate movement of the front and back folding plates 208, 210 toward the closed configuration of the folding device. FIG. 16 illustrates the partially folded condition of the pants 20 at angular position B of the drum. At angular position C of the drum 202, the folding plates 208, 210 (and hence the transverse retention plates 302 connected to the front folding plate) are folded further inward toward the closed configuration of the folding device 206. FIG. 17 illustrates the further folded condition of the pants 20 at angular position C.

As the front and back shafts 258, 260 of the folding device 206 rotate to move the folding plates 208, 210 toward the closed configuration of the folding device 206, the suction device 352 is moved relative to the inner ends 212, 214 of the folding plates, and more particularly radially inward relative to the folding device and drum 202, via the collars 374, lever arms 376, corresponding links 378 and slides 370 that couple the suction device to movement of the front folding plate. The suction device 352, still operating in its vacuum mode, continues to draw the central region 26 of the pants 20 toward the inlet 358 of the vacuum duct 356 to generally hold the central region of the pants outward of the inner ends 212, 214 of the folding plates 208, 210 to inhibit bunching of the central region between the folding plates. Concurrently, as illustrated by comparing FIG. 17 to FIG. 15, the transverse retention plates 302 are slidably moved on the cross-bars 306 transversely inward toward the back folding plate 210 by the longitudinal link 314, slide 310 and transverse links 312 that operatively couple transverse movement of the retention plates 302 to the folding movement of the back folding plate.

Figure 18:
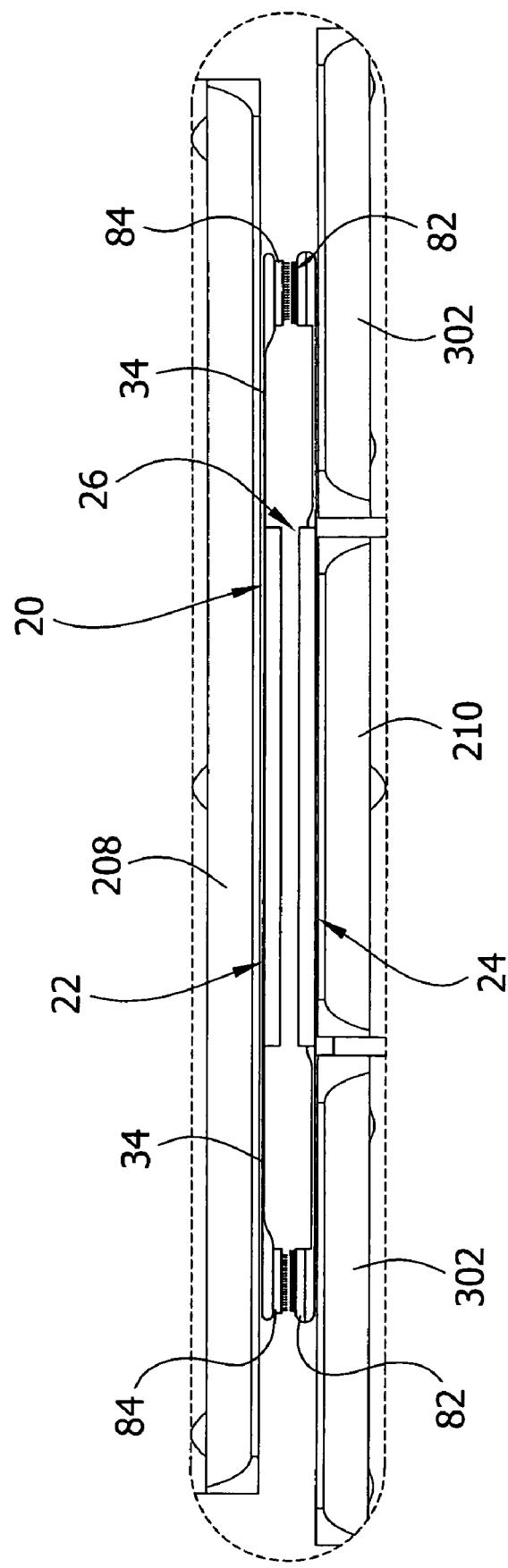
FIG. 18 is an enlarged end view of the folding device of FIG. 15 with the folding device in its closed configuration so that the absorbent undergarment is folded and pre-fastened.

Upon further rotation of the drum 202 to angular position D, the front and back folding plates 208, 210 are in opposed relationship with each other in the closed configuration of the folding device 206. Accordingly, the training pants 20 are folded so that the front and back waist regions (i.e., the first and second end regions) 22, 24 of the pants are in opposed relationship with each other. The transverse retention plates 302 have been moved sufficiently transversely inward such that the fastening portions at the back waist region 24 (e.g., fastening components 82) are in opposed relationship with the fastening portions at the front waist region 22 (e.g., fastening components 84). As a result, the fastening portions (e.g., fastening components 82, 84) are brought together for fastening engagement with each other as illustrated in FIG. 18 to pre-fasten the pants 20 in the closed configuration of the folding device 206. As illustrated in FIG. 19, a portion of the central region 26 of the pants 20 is positioned by the suction device 352 outward of the inner ends 212, 214 of the folding plates 208, 210 in the closed configuration of the folding device.

With further reference to FIG. 6, as the drum 202 rotates further towards angular position E, vacuum pressure to the back folding plate 210 and transverse retention plates 302 is decreased, and more suitably blocked altogether by the vacuum shoe. The cam box 262 drives rotation of the front and back shafts 258, 260 to initiate movement of the front and back folding plates 208, 210 back toward the open configuration of the folding device 206. The folded and now pre-fastened training pants 20 are still drawn against and retained on the cover panel 272 of the front folding plate 208 as the folding device 206 is moved toward its open configuration as illustrated at angular positions E and F of FIG. 6. At angular position G of the drum 202, the folding device 206 is in its fully open configuration, with the folded and pre-fastened training pants 20 laying generally flat against and being held on the cover panel 272 of the front folding plate 208.

The drum 202 rotates further to angular position H at which the folding plates 258, 260, in the open configuration of the folding device 206, are in generally opposed relationship with a suitable transfer device, such as the conventional vacuum box conveyor 390 illustrated in FIG. 6. The vacuum box conveyor 390 draws the pre-fastened training pants 20 off of the folding device 206 and transfers the training pants downstream of the folding device for further processing. In one embodiment, the vacuum pressure of the vacuum box conveyor 290 is suitably greater than that holding the training pants 20 on the front folding plate 208 so as to draw the training pants away from the front folding plate. Alternatively, or additionally, it is understood that the vacuum pressure to the interior chamber of the front folding plate 208 may be decreased or even blocked by the vacuum shoe to further facilitate the transfer of the training pants 20 to the transfer device 390.

In another embodiment, the transfer device 390 may comprise a simple (e.g., non-vacuum) conveyor or other transfer device and the training pants 20 may be transferred onto the conveyor by gravity, or by operating the front folding plate 208 in a blowing mode to blow pressurized gas out through the cover panel 272 of the back folding plate, thereby urging the training pants away from the folding plate and onto the conveyor, or by other suitable techniques.

The folding plates 208, 210 suitably remain in the open configuration of the folding device 206 as the drum 202 rotates through angular positions H, I and J until the drum has completed a full 360 degree rotation and returns to angular position A.

While the fastening portions (e.g., fastening components 82) at the back waist region 24 of the pants are moved transversely relative to the back folding plate 210 (and more particularly transversely inward, closer to the back folder plate) for alignment with the fastening portions (e.g., fastening components 84) at the front waist region 22, it is understood that transverse retention members may be provided for the front folding plate 208 for moving the front fastening portions relative to the front folding plate. For example, the back fastening portions of the pants 20 may be retained against movement relative to the back folding plate 210 and the front (transversely folded) fastening portions may be retained on transverse retention members adjacent the front folding plate and moved by the retention members transversely outward away from the front folding plate 208, thereby stretching the side panels 34 of the pants, to align the front and back fastening portions of the pants for engagement.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. Apparatus for mechanically fastening an absorbent undergarment to reconfigure the undergarment from a partially assembled, unfastened configuration to a pre-fastened configuration during the initial manufacturing thereof, the absorbent undergarment having a longitudinal axis, a lateral axis, a first end region, a second end region and a central region extending longitudinally between and interconnecting the first and second end regions, a first fastening portion generally at the first end region and a second fastening portion generally at second end region in longitudinally spaced relationship with the first fastening portion and engageable therewith to secure the absorbent garment in its pre-fastened configuration, said first and second fastening portions being unfastened and said undergarment being generally unfolded in said partially assembled configuration, said undergarment being folded and said first and second fastening portions being engaged with each other in said pre-fastened configuration of the undergarment, said apparatus comprising;

a transport device driven to move in a transport direction;

a longitudinal folding device carried by the transport device in the transport direction, the longitudinal folding device being configurable relative to the transport device between an open configuration in which the longitudinal folding device receives an absorbent undergarment in its partially assembled configuration, and a closed configuration in which the absorbent undergarment is folded longitudinally by the folding device, said longitudinal folding device comprising first and second folding plates moveable relative to each other between the open and closed configurations of the folding device, in the closed configuration of the folding device the folding plates being in opposed relationship with each other and in the open configuration of the folding device the plates being out of opposed relationship with each other, the folding plates each having an inner end and an outer end, the inner ends of the folding plates being nearer to each other than the outer ends of the folding plates in the open configuration of the folding device, said inner ends of the folding plates being spaced from each other in said open configuration of the folding device, the first folding plate for retaining the first end region of the absorbent undergarment thereon and the second plate for retaining the second end region of the absorbent undergarment thereon such that the central region of the absorbent undergarment is generally adjacent the inner ends of the folding plates and spans the spacing between said inner ends, the folding device being configured such that in the closed configuration of the folding plates the first and second fastening portions of the undergarment are brought together for fastening engagement therebetween; and a holding device separate from the first and second folding plates and disposed generally intermediate the inner ends of the folding plates, said holding device for positioning the central region of the absorbent undergarment longitudinally outward of the inner ends of the folding plates in the closed configuration of the folding device.

2. The apparatus set forth in claim 1 wherein the holding device comprises a suction device operable in a vacuum mode to draw the central region of the absorbent garment toward said suction device upon movement of the folding plates from the open configuration of the folding device to its closed configuration.

3. The apparatus set forth in claim 1 wherein the holding device is moveable relative to the first and second folding plates in response to movement of the folding plates between the open and closed configurations of the folding device.

4. The apparatus set forth in claim 3 wherein the holding device is operatively connected to the first folding device such that movement of the first folding device between the open and closed configurations of the folding device drives movement of the holding device relative to the first and second folding plates.

5. The apparatus set forth in claim 3 wherein the holding device is operatively connected to the second folding device such that movement of the second folding device between the open and closed configurations of the folding device drives movement of the holding device relative to the first and second folding plates.

6. Apparatus for mechanically fastening an absorbent undergarment to reconfigure the undergarment from a partially assembled, unfastened configuration to a pre-fastened configuration during the initial manufacturing thereof, the absorbent undergarment having a longitudinal axis, a lateral axis, a first end region, a second end region and a central region extending longitudinally between and interconnecting the first and second end regions, a first fastening portion generally at the first end region and a second fastening portion generally at second end region in longitudinally spaced relationship with the first fastening portion and engageable therewith to secure the absorbent garment in its pre-fastened configuration, said first and second fastening portions being unfastened and said undergarment being generally unfolded in said partially assembled configuration, said undergarment being folded and said first and second fastening portions being engaged with each other in said pre-fastened configuration of the undergarment, said apparatus comprising;

a transport device driven to move in a transport direction;

a longitudinal folding device carried by the transport device in the transport direction, the longitudinal folding device being configurable relative to the transport device between an open configuration in which the longitudinal folding device receives an absorbent undergarment in its partially assembled configuration, and a closed configuration in which the absorbent undergarment is folded longitudinally by the folding device, said longitudinal folding device comprising first and second folding plates moveable relative to each other between the open and closed configurations of the folding device, in the closed configuration of the folding device the folding plates being in opposed relationship with each other and in the open configuration of the folding device the plates being out of opposed relationship with each other, the folding plates each having an inner end and an outer end, the inner ends of the folding plates being nearer to each other than the outer ends of the folding plates in the open configuration of the folding device, said inner ends of the folding plates being spaced from each other in said open configuration of the folding device, the first folding plate for retaining the first end region of the absorbent undergarment thereon and the second plate for retaining the second end region of the absorbent undergarment thereon such that the central region of the absorbent undergarment is generally adjacent the inner ends of the folding plates and spans the spacing between said inner ends, the folding device being configured such that in the closed configuration of the folding plates the first and second fastening portions of the undergarment are brought together for fastening engagement therebetween;

a holding device separate from the first and second folding plates and disposed generally intermediate the inner ends of the folding plates, said holding device for positioning the central region of the absorbent undergarment longitudinally outward of the inner ends of the folding plates in the closed configuration of the folding device; and a transverse retention member generally adjacent to the second folding plate for retaining the second fastening portion of the undergarment thereon upon movement of the folding plates from the open configuration of the folding device to the closed configuration thereof, said transverse retention member being moveable at least transverse to the second folding plate to facilitate alignment of the second fastening portion of the undergarment with the first fastening portion of the undergarment for fastening engagement therebetween in the closed configuration of the folding device.

7. The apparatus set forth in claim 6 wherein the transverse retention member is connected to the second folding plate for conjoint movement with the second folding plate between the open and closed configurations of the folding device.

8. The apparatus set forth in claim 7 wherein the transverse retention member is connected to the second folding plate by at least one transversely extending cross-bar, the transverse retention member being slidably mounted on the cross-bar for transverse sliding movement of the transverse retention member relative to the second folding plate.

9. The apparatus set forth in claim 6 wherein the transverse retention member comprises a porous cover panel and an interior chamber in fluid communication with the porous cover panel, the apparatus further comprising a vacuum source in fluid communication with the interior chamber of the transverse retention member, said retention member being operable in a vacuum mode in which the vacuum source draws a vacuum on the porous cover panel of the transverse retention member via the interior chamber thereof to draw toward and retain on said cover the second fastening portion of the undergarment.

10. The apparatus set forth in claim 6 wherein the absorbent undergarment has a pair of laterally spaced first fastening portions generally at said first end region and a corresponding pair of laterally spaced second fastening portions generally at said second end region, the transverse retention member comprising a first transverse retention member adjacent one transverse side of the second folding plate for retaining thereon one of the second fastening portions, the folding device further comprising a second transverse retention member adjacent an opposite transverse side of the second folding plate for retaining the other one of the second fastening portions thereon during movement of the folding plates from the open to the closed configuration of the folding device.

11. The apparatus set forth in claim 6 wherein the transverse retention member is responsive to movement of the second folding plate between the open and closed configurations of the folding device to move relative to said second folding plate.

12. The apparatus set forth in claim 11 wherein the transverse retention member is operatively connected to the second folding plate such that movement of the second folding plate between the open and closed configurations of the folding device drives movement of the transverse retention member relative to the second folding plate.

13. Apparatus for mechanically fastening an absorbent undergarment to reconfigure the undergarment from a partially assembled, unfastened configuration to a pre-fastened configuration during the initial manufacturing thereof, the absorbent undergarment having a longitudinal axis, a lateral axis, a first end region, a second end region and a central region extending longitudinally between and interconnecting the first and second end regions, a first fastening portion generally at the first end region and a second fastening portion generally at the second end region in longitudinally spaced relationship with the first fastening portion and engageable therewith to secure the absorbent garment in its pre-fastened configuration, said first and second fastening portions being unfastened and said undergarment being generally unfolded in said partially assembled configuration, said undergarment being folded and said first and second fastening portions being engaged with each other in said pre-fastened configuration of the undergarment, said apparatus comprising;

a transport device driven to move in a transport direction;

a longitudinal folding device carried by the transport device in the transport direction, the longitudinal folding device being configurable relative to the transport device between an open configuration in which the longitudinal folding device receives an absorbent undergarment in its partially assembled configuration, and a closed configuration in which the absorbent undergarment is folded longitudinally by the folding device, said longitudinal folding device comprising first and second folding plates moveable relative to each other between the open and closed configurations of the folding device, in the closed configuration of the folding device the folding plates being in opposed relationship with each other and in the open configuration of the folding device the plates being out of opposed relationship with each other; and a transverse retention member generally adjacent to the second folding plate for retaining the second fastening portion of the undergarment thereon upon movement of the folding plates from the open configuration of the folding device to the closed configuration thereof, said transverse retention member being moveable at least transverse to the second folding plate to adjust the transverse position of the second fastening portion of the undergarment relative to the second folding plate to facilitate fastening engagement of the second fastening portion of the undergarment with the first fastening portion thereof in the closed configuration of the folding device.

14. The apparatus set forth in claim 13 wherein the transverse retention member is connected to the second folding plate for conjoint movement with the second folding plate between the open and closed configurations of the folding device.

15. The apparatus set forth in claim 14 wherein the transverse retention member is connected to the second folding plate by at least one transversely extending cross-bar, the transverse retention member being slidably mounted on the at least one cross-bar for transverse sliding movement of the transverse retention member relative to the second folding plate.

16. The apparatus set forth in claim 13 wherein the transverse retention member comprises a porous cover panel and an interior chamber in fluid communication with the porous cover panel, the apparatus further comprising a vacuum source in fluid communication with the interior chamber of the transverse retention member, said retention member being operable in a vacuum mode in which the vacuum source draws a vacuum on the porous cover panel of the transverse retention member via the interior chamber thereof to draw toward and retain on said cover panel the second fastening portion of the undergarment.

17. The apparatus set forth in claim 13 wherein the absorbent undergarment has a pair of laterally spaced first fastening portions generally at said first end region and a corresponding pair of laterally spaced second fastening portions generally at said second end region, the transverse retention member comprising a first transverse retention member adjacent one transverse side of the second folding plate for retaining thereon one of the second fastening portions, the folding device further comprising a second transverse retention member adjacent an opposite transverse side of the second folding plate for retaining retain the other one of the second fastening portions thereon during movement of the folding plates from the open to the closed configuration of the folding device.

18. The apparatus set forth in claim 13 wherein the transverse retention member is responsive to movement of the second folding plate between the open and closed configurations of the folding device to move at least transverse to said second folding plate.

19. The apparatus set forth in claim 18 wherein the transverse retention member is operatively connected to the second folding plate such that movement of the second folding plate between the open and closed configurations of the folding device drives movement of the transverse retention member relative to the second folding plate.

* * * * *